(12) United States Patent
Castro et al.

(10) Patent No.: US 8,933,256 B2
(45) Date of Patent: Jan. 13, 2015

(54) CATALYSTS

(75) Inventors: Pascal Castro, Helsinki (FI); Luigi Resconi, Ferrara (IT); Lauri Huhtanen, Loviisa (FI)

(73) Assignee: Borealis AG, Vienna (AT)

( * ) Notice: Subject to any disclaimer, the term of this patent is extended or adjusted under 35 U.S.C. 154(b) by 0 days.

(21) Appl. No.: 13/806,421

(22) PCT Filed: Jun. 29, 2011

(86) PCT No.: PCT/EP2011/060921
§ 371 (c)(1),
(2), (4) Date: Feb. 25, 2013

(87) PCT Pub. No.: WO2012/001052
PCT Pub. Date: Jan. 5, 2012

(65) Prior Publication Data
US 2013/0289229 A1    Oct. 31, 2013

(30) Foreign Application Priority Data
Jul. 1, 2010    (EP) .................................... 10168150

(51) Int. Cl.
| | | |
|---|---|---|
| C08F 4/642 | (2006.01) | |
| C08F 4/6592 | (2006.01) | |
| C08F 10/00 | (2006.01) | |
| C07F 17/00 | (2006.01) | |
| C08F 4/659 | (2006.01) | |
| C08F 110/06 | (2006.01) | |

(52) U.S. Cl.
CPC ......... *C08F 4/65912* (2013.01); *C08F 4/65927* (2013.01); *C07F 17/00* (2013.01); *C08F 110/06* (2013.01); *Y10S 526/943* (2013.01)
USPC ............. 556/53; 502/103; 502/152; 526/160; 526/348; 526/943

(58) Field of Classification Search
CPC ............... C08F 4/6592; C08F 4/65927; C08F 4/65912; C08F 10/00; C07F 17/00
USPC ............. 526/160, 943, 348; 556/53; 502/103, 502/152
See application file for complete search history.

(56) References Cited

FOREIGN PATENT DOCUMENTS

| | | |
|---|---|---|
| EP | 1567565 B1 | 1/2008 |
| WO | WO94/14856 A1 | 7/1994 |
| WO | WO95/12622 A1 | 5/1995 |
| WO | WO03/051934 A2 | 6/2003 |
| WO | WO2004/050724 A1 | 6/2004 |
| WO | WO2005/058916 A2 | 6/2005 |
| WO | WO2006/060544 A1 | 6/2006 |
| WO | WO2006/097497 A1 | 9/2006 |
| WO | WO2007/116034 A1 | 10/2007 |
| WO | WO2009/054832 A1 | 4/2009 |
| WO | 2010077230 A1 | 7/2010 |
| WO | WO2011/076780 A1 | 6/2011 |

OTHER PUBLICATIONS

International Search Report and Written Opinion for Application No. PCT/EP2011/060920 dated Jul. 28, 2011.
International Search Report and Written Opinion for Application No. PCT/EP2011/060921 dated Jul. 25, 2011.
Neudeck H K, Aromatische Spirane, 14. Mitt. Not 1 3/4 Darstellung Von 2,2'-Spirobi-(S-Hydrindacen) Und Seinen Vorstufen, Monatshefte Fur Chemie, Springer Verlag Wien, AT LNKD-DOI:10. 1007/ BF00809674, vol. 118, No. 5, Jan. 1, 1987, pp. 627-657, XP000981981 ISSN: 0026-9247.
Non-final Office Action, dated Feb. 14, 2014, received in connection with related U.S. Appl. No. 13/806,386.
Notice of Allowance from U.S. Appl. No. 13/806,386 dated Jun. 27, 2014.

*Primary Examiner* — Caixia Lu
(74) *Attorney, Agent, or Firm* — Meunier Carlin & Curfman, LLC

(57) ABSTRACT

A complex of formula (I): wherein M is zirconium or hafnium; each X is a sigma ligand; L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-hydrocarbyl, tri(C1-C20-alkyl)silyl, C6-C20-aryl, C7-C20-arylalkyl or C7-C20-alkylaryl; each R$^1$ is a C4-C20 hydrocarbyl radical branched at the β-atom to the cyclopentadienyl ring, optionally containing one or more heteroatoms belonging to groups 14-16, or is a C3-C20 hydrocarbyl radical branched at the β-atom to the cyclopentadienyl ring where the β-atom is an Si-atom; n is 0-3; each R$^{18}$ is the same or different and may be a C1-C20 hydrocarbyl radical optionally containing one or more heteroatoms belonging to groups 14-16; each R$^4$ is a hydrogen atom or a C$_{1-6}$-hydrocarbyl radical; each W is a 5 or 6 membered aryl or heteroaryl ring wherein each atom of said ring is optionally substituted with an R$^5$ group each R$^5$ is the same or different and is a C1-C20 hydrocarbyl radical optionally containing one or more heteroatoms belonging to groups 14-16; and optionally two adjacent R$^5$ groups taken together can form a further mono or multicyclic ring condensed to W optionally substituted by one or two groups R$^5$.

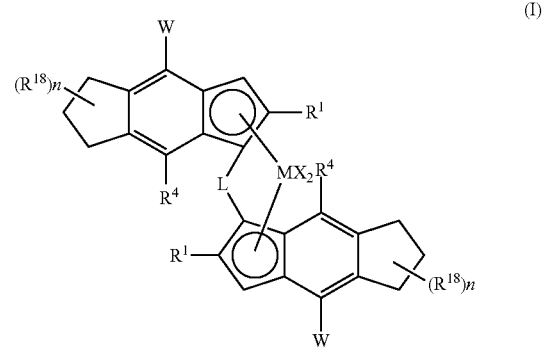

11 Claims, No Drawings

CATALYSTS

This invention relates to complexes comprising bridged bis indenyl Π-ligands useful in the formation of olefin polymerisation catalysts, as well as the use thereof in olefin polymerisation, in particular for polymerising propylene. The invention especially relates to catalysts which comprise certain bridged bis indenyl complexes in solid form, e.g. supported or ideally in solid but unsupported form. Certain complexes of the invention are also new and form still yet further aspects of the invention as do certain processes for their manufacture.

Metallocene catalysts have been used to manufacture polyolefins for many years. Countless academic and patent publications describe the use of these catalysts in olefin polymerisation. Metallocenes are now used industrially and polyethylenes and polypropylenes in particular are often produced using cyclopentadienyl based catalyst systems with different substitution patterns.

These metallocenes can be used in solution polymerisation but results of such polymerisations have generally been poor. These metallocenes are therefore conventional supported on a carrier such as silica. Research has found that heterogeneous catalysis (in which the catalyst particles do not dissolve in the reaction medium) gives rise to better polymer products than homogeneous catalysis (in solution). The use therefore of a support is common place. Despite several years of development of this catalyst technology, there is still room for improved activity, and improved polymer particle formation.

In WO03/051934, the inventors proposed an alternative form of catalyst which is provided in solid form but does not require a conventional external carrier material such as silica. The invention is based on the finding that a homogeneous catalyst system containing an organometallic compound of a transition metal can be converted, in a controlled way, to solid, uniform catalyst particles by first forming a liquid/liquid emulsion system, which comprises as the dispersed phase, said solution of the homogeneous catalyst system, and as the continuous phase a solvent immiscible therewith, and then solidifying said dispersed droplets to form solid particles comprising the said catalyst.

The invention described in WO03/051934 enabled the formation of solid spherical catalyst particles of said organotransition metal catalyst without using e.g. external porous carrier particles, such as silica, normally required in the art. Thus, problems relating to catalyst silica residues can be solved by this type of catalyst. Further, it could be seen that catalyst particles having improved morphology, will give, due to the replica effect, polymer particles having improved morphology as well.

Although a lot of work has been done in the field of metallocene catalysts, both with conventional supported catalysts as well with solid catalysts prepared according to the principles as described in said WO03/051934, there still remain some problems, which relate especially to the productivity or activity of the catalysts. The productivity or activity has been found to be relatively low, especially when polymers of low melt index (MI) (i.e. high molecular weight, $M_w$) are produced using known catalysts.

There remains a need therefore to find new catalysts for olefin polymerisation, which are able to produce polymers with desired properties and which have high activity and/or productivity. Further, it is highly desired in many polymer applications that inorganic residues, e.g. silica residues, in the final product are reduced as much as possible.

A further problem relating to the catalyst activity seems to be that activity of known catalysts is not at a sufficiently high level over a broad range of hydrogen concentration, i.e. where the skilled man is producing lower or higher Mw polymers. Thus, catalysts having broader operating windows, i.e. good activity over a broad range of molecular weights of the polymer, are highly desired. Further, the problems with conventional silica supported catalysts, i.e. low productivity, have to be avoided. Producing polymers with high isotacticity and hence higher crystallinity and thermal resistance is also desirable.

In particular, the present inventors were faced with the problem of manufacturing a polymer with high molecular weight (i.e. enabling the formation of polymer components with low melt index). This had to be achieved whilst maintaining high catalyst activity and productivity. At the same time the present inventors were faced with the problem of manufacturing a polypropylene homopolymer with higher crystallinity and thermal resistance.

As a consequence, the inventors set out to develop a catalyst having a superior polymerisation behaviour than the above mentioned polymerisation catalyst systems regarding one or more of the following characteristics:

higher isotacticity, resulting in higher crystallinity and thermal resistance;
higher activity and productivity.

It was also important to improve or maintain performance in producing high molecular weight polypropylene ($MFR_2$<1).

The present inventors have now found a new class of olefin polymerisation catalysts, which are able to solve the problems disclosed above, and which catalysts are not previously described in the art. The invention combines known supporting techniques, for example using silica as described in WO2006/097497, or the catalyst emulsion/solidification techniques of WO03/051934, with a specific group of metallocene complexes based on a bis-indenyl structure in which the indenyl group carries a five-membered ring (thus forming a trihydroindacenyl ligand). Also, the 2-position of the indenyl ring must carry a group, branched at the β carbon to the cyclopentadienyl ring. This combination surprisingly results in catalysts having high activity, e.g. improved activity over the known catalysts prepared according to WO03/051934. Moreover, the features of the catalyst of the invention enable the formation of polymers having a broad range of molecular weights, especially, very high molecular weight products. Further, as a special embodiment, the invention further provides a catalyst, where no silica support material needs to be used. This avoids any problems relating to the use of the conventional supported catalysts, such as silica supported catalysts.

These polymers operate well over a broad range of hydrogen pressures, and form high isotacticity polymers.

Complexes similar to those used in the manufacture of the catalysts of the invention are disclosed in the prior art but they do not show the same advantageous combination of improved properties. Moreover, the importance of the branch at the β-position of the substituent on the 2-position of the indenyl ligand is not appreciated. Moreover, the complexes of the invention generally represent a selection from the very broad disclosures of metallocene catalysts in the prior art.

In WO2006/097497 some broadly defined metallocene complexes are disclosed based on bis indenyl structures in which a non aromatic ring is bound to the 6-membered ring of the indenyl group. Some compounds with a 5 membered ring attached to the indenyl ring (e.g. those of formula II of WO2006/097497) are disclosed but these metallocenes do not show all required properties. Moreover, the importance of a branched group at the β-position of the substituent on the 2-position of the indenyl ligand is not appreciated.

WO2005/058916 primarily describes asymmetric metallocenes in which the 2-position substituents are different.

WO2009/054832 discloses conventionally supported metallocene catalysts which are branched at the 2-position of the cyclopentadienyl ring in at least one of the ligands making up the catalyst. The exemplified species are however, bis-indenyl catalysts It has now surprisingly been found that using the particular complexes described below in solid form, the resulting catalysts comprehensively outperform known catalysts prepared according to the method of WO03/051934. Moreover, these catalysts outperform the preferred metallocenes of WO2006/097497 even when these are formulated using the techniques of WO03/051934. This is an entirely surprising result.

Thus, viewed from one aspect the invention provides a catalyst comprising:

(i) a complex of formula (I):

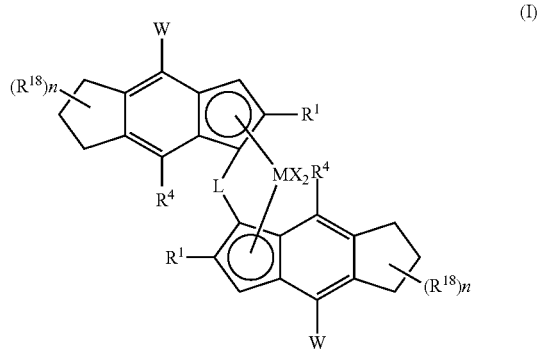

wherein

M is zirconium or hafnium;

each X is a sigma ligand;

L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-hydrocarbyl, tri(C1-C20-alkyl)silyl, C6-C20-aryl, C7-C20-arylalkyl or C7-C20-alkylaryl;

each $R^1$ is a C4-C20 hydrocarbyl radical branched at the β-atom to the cyclopentadienyl ring, optionally containing one or more heteroatoms belonging to groups 14-16, or is a C3-C20 hydrocarbyl radical branched at the β-atom to the cyclopentadienyl ring where the β-atom is an Si-atom;

n is 0-3;

each $R^{18}$ is the same or different and may be a C1-C20 hydrocarbyl radical optionally containing one or more heteroatoms belonging to groups 14-16;

each $R^4$ is a hydrogen atom or a $C_{1-6}$-hydrocarbyl radical;

each W is a 5 or 6 membered aryl or heteroaryl ring wherein each atom of said ring is optionally substituted with an $R^5$ group;

each $R^5$ is the same or different and is a C1-C20 hydrocarbyl radical optionally containing one or more heteroatoms belonging to groups 14-16; and optionally two adjacent $R^5$ groups taken together can form a further mono or multicyclic ring condensed to W optionally substituted by one or two groups $R^5$;

and (ii) a cocatalyst comprising an organometallic compound of a Group 13 metal.

The catalyst of the invention is in solid particulate form either supported on an external carrier material, like silica or alumina, or, in a particularly preferred embodiment, is free from an external carrier. Ideally, the catalyst is obtainable by a process in which (a) a liquid/liquid emulsion system is formed, said liquid/liquid emulsion system comprising a solution of the catalyst components (i) and (ii) dispersed in a solvent so as to form dispersed droplets; and (b) solid particles are formed by solidifying said dispersed droplets.

Viewed from another aspect the invention provides a process for the manufacture of a catalyst as hereinbefore defined comprising obtaining a complex of formula (I) and a cocatalyst as hereinbefore described;

forming a liquid/liquid emulsion system, which comprises a solution of catalyst components (i) and (ii) dispersed in a solvent, and solidifying said dispersed droplets to form solid particles.

Viewed from another aspect the invention provides the use in olefin polymerisation of a catalyst as hereinbefore defined.

Viewed from another aspect the invention provides a process for the polymerisation of at least one olefin comprising reacting said at least one olefin with a catalyst as hereinbefore described.

DEFINITIONS

Throughout the description the following definitions are employed.

By free from an external carrier is meant that the catalyst does not contain an external support, such as an inorganic support, for example, silica or alumina, or an organic polymeric support material.

For nomenclature purposes, the following numbering scheme will be used for the trihydro-s-indacenyl backbone of the bridged ligand. L is a divalent bridge and has the same definition as described above. It should be noted that trihydro-s-indacenyl can be considered as 5,6-trimethyleneindenyl.

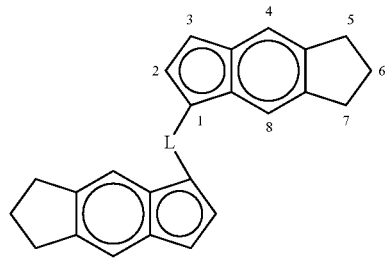

The term $C_{1-20}$ hydrocarbyl group therefore includes $C_{1-20}$ alkyl, $C_{2-20}$ alkenyl, $C_{2-20}$ alkynyl, $C_{3-20}$ cycloalkyl, $C_{3-20}$ cycloalkenyl, $C_{6-20}$ aryl groups, $C_{7-20}$ alkylaryl groups or $C_{7-20}$ arylalkyl groups or of course mixtures of these groups such as cycloalkyl substituted by alkyl.

Unless otherwise stated, preferred $C_{1-20}$ hydrocarbyl groups are $C_{1-20}$ alkyl, $C_{4-20}$ cycloalkyl, $C_{5-20}$ cycloalkylalkyl groups, $C_{7-20}$ alkylaryl groups, $C_{7-20}$ arylalkyl groups or $C_{6-20}$ aryl groups, especially $C_{1-10}$ alkyl groups, $C_{6-10}$ aryl groups, or $C_{7-12}$ arylalkyl groups, e.g. $C_{1-8}$ alkyl groups. Most especially preferred hydrocarbyl groups are methyl, ethyl, propyl, isopropyl, tertbutyl, isobutyl, $C_{5-6}$-cycloalkyl, cyclohexylmethyl, phenyl or benzyl.

The term halo includes fluoro, chloro, bromo and iodo groups, especially chloro groups, when relating to the complex definition.

The term heterocyclic group means a preferably monocyclic non aromatic ring structure comprising at least one heteroatom, e.g. piperidinyl or piperazinyl.

The term heteroaryl means a preferably monocyclic aromatic ring structure comprising at least one heteroatom. Preferred heteroaryl groups have 1 to 4 heteroatoms selected from O, S and N. Preferred heteroaryl groups include furanyl, thiophenyl, oxazole, thiazole, isothiazole, isooxazole, triazole and pyridyl.

Any group including "one or more heteroatoms belonging to groups 14-16" preferably means O, S or N. N groups may present as —NH— or —NR"— where R" is C1-10 alkyl. There may, for example, be 1 to 4 heteroatoms.

The oxidation state of the metal ion is governed primarily by the nature of the metal ion in question and the stability of the individual oxidation states of each metal ion.

It will be appreciated that in the complexes of the invention, the metal ion M is coordinated by ligands X so as to satisfy the valency of the metal ion and to fill its available coordination sites. The nature of these σ-ligands can vary greatly.

Catalyst activity is defined in this application to be the amount of polymer produced/g catalyst/h. Catalyst metal activity is defined here to be the amount of polymer produced/g Metal/h. The term productivity is also sometimes used to indicate the catalyst activity although herein it designates the amount of polymer produced per unit weight of catalyst.

DETAILED DESCRIPTION OF INVENTION

The complexes and hence catalysts of the invention are based on formula (I) as hereinbefore defined which, inter alia, combines the use of the trihydroindacenyl tricyclic ring structure with a substituent at the 2-position that is branched β to the cyclopentadienyl ring.

The two multicyclic ligands making up the complex of formula (I) are preferably identical and hence the complex of formula (I) may be symmetrical. The complexes of the invention may be in their meso or racemic forms (or a mixture thereof). Preferably, the racemic (rac) form is used.

M is preferably Zr or Hf, especially Zr.

Each X, which may be the same or different, is preferably a hydrogen atom, a halogen atom, a R, OR, $OSO_2CF_3$, OCOR, SR, $NR_2$ or $PR_2$ group wherein R is a linear or branched, cyclic or acyclic, C1-C20-alkyl, C2-C20 alkenyl, C2-C20 alkynyl, C6-C20-aryl, C7-C20-alkylaryl or C7-C20-arylalkyl radical; optionally containing heteroatoms belonging to groups 14-16. R is preferably a $C_{1-6}$ alkyl, phenyl or benzyl group.

Most preferably each X is independently a hydrogen atom, a halogen atom, $C_{1-6}$-alkoxy group or an R group, e.g. preferably a $C_{1-6}$-alkyl, phenyl or benzyl group. Most preferably X is chlorine or a methyl radical. Preferably both X groups are the same.

L is preferably a bridge comprising a heteroatom, such as silicon or, germanium, e.g. —$SiR^6_2$—, wherein each $R^6$ is independently C1-C20-alkyl, C6-C20-aryl or tri(C1-C20-alkyl)silyl-residue, such as trimethylsilyl. More preferably $R^6$ is $C_{1-6}$-alkyl, especially methyl. Most preferably, L is a dimethylsilyl or diethyl bridge.

$R^1$ is branched β to the cyclopentadienyl ring. By branched β to the cyclopentadienyl ring is meant that the second atom from the cyclopentadienyl ring must be secondary or tertiary, preferably secondary. This atom is preferably Si or C but is most preferably C. The $R^1$ radical preferably comprises at least 4 carbon atoms in the chain, or alternatively at least 6 carbon atoms. Where an Si atom is present β to the cyclopentadienyl ring it is possible for there to be three carbon atoms present in the $R^1$ group in addition to the Si atom at the beta position.

It will also be appreciated that where a cyclic group such as a cycloalkyl group, heterocyclic, heteroaryl or aryl group is present at the atom β to the cyclopentadienyl then there is a branch present.

The $R^1$ group may contain one or more heteroatoms belonging to groups 14-16, e.g. O, N or S. There may be 1 to 3 of such heteroatoms. These heteroatoms may be positioned to allow formation of a heterocyclic or heteroaryl group in the $R^1$ group e.g. a $CH_2$-heteroaryl or $CH_2$-heterocyclic group having 3-10 carbon atoms and one to three heteroatoms.

It is preferred that heteroatoms in the $R^1$ group (other than Si at the beta position as discussed below) are not positioned at the atoms α, β, or γ to the cyclopentadienyl ring. Thus, the backbone atom positioned α to the ring is preferably C, the backbone atom β to the ring is C or Si and the atoms attached to β position (other than hydrogen) are C atoms. Heteroatoms, if present should be positioned at least delta to the cyclopentadienyl ring. Preferably there are no heteroatoms present in groups $R^1$.

Where there is an Si atom β to the cyclopentadienyl ring it is preferred if there are no other heteroatoms present in the $R^1$ group. Where Si interrupts the carbon chain β to the cyclopentadienyl ring, preferred such groups include $CH_2$— $SiR^{10}_3$ where $R^{10}$ is a $C_{1-6}$ alkyl group, e.g. methyl.

Preferably $R^1$ is a C4-20 hydrocarbyl group, more preferably C4-C12 hydrocarbyl branched β to the cyclopentadienyl ring, optionally containing one or more heteroatoms belonging to groups 14-16.

Radical $R^1$ is preferably a suitably branched C4-C20-alkyl, a $CH_2$-cycloalkyl group having 4 to 12 carbon atoms or a $CH_2$-aryl radical containing from 7 to 11 carbon atoms.

In a preferred embodiment, $R^1$ is the group —$CH_2$—$R^{1'}$, i.e. the link to the cyclopentadienyl ring is via a methylene group and $R^{1'}$ represents the remainder of the $R^1$ group, e.g. a C3-19 hydrocarbyl group optionally containing one or more heteroatoms belonging to groups 14-16 or a C2-19 hydrocarbyl group where the atom to the cyclopentadienyl ring is Si.

In particular, $R^{1'}$ represents a $C_{3-7}$-cycloalkyl group (optionally susbstituted by $C_{1-6}$-alkyl), a $C_{6-10}$-aryl group, especially phenyl or an $C_{3-8}$-alkyl group (such that the beta position to the cyclopentadienyl is branched). In some embodiments the $R^{1'}$ group can represent a heteroaryl or heterocyclic group having 2 to 8 carbon atoms and one to three heteroatoms (e.g. S, N or O). Heteroatoms, if present, should preferably be positioned at least delta to the cyclopentadienyl ring.

Suitable heteroaryl groups include pyrrolyl, indolyl, furanyl, oxazole, thiazole, isothiazole, isooxazole, triazole and pyridyl. Suitable heterocyclic groups include piperidinyl and piperazinyl.

In a further preferred embodiment therefore, $R_1$ is a group $CH_2$—$C(R_3)_{3-q}(H)_q$ wherein each $R_3$ is a $C_{1-6}$-alkyl group or together two $R_3$ groups form a $C_{3-7}$— cycloalkyl ring. The subscript q can be 1 or 0.

More preferably $R^1$ is a suitably branched $C_{4-10}$-alkyl radical, preferably a suitably branched $C_{4-8}$-alkyl radical. $R^1$ is ideally an isobutyl or —$CH_2CH(Me)(Et)$ group. Alternatively, $R^1$ is —$CH_2C_6H_{11}$ where $C_6H_{11}$ is cyclohexyl, $CH_2C_6H_{11}(Me)$ where the cyclohexyl is substituted by methyl or —$CH_2C_6H_5$ (benzyl).

If substituted by a group $R^{18}$, it is preferred if there are 1 to 3, preferably 1 or 2 such groups present. The 5-membered non aromatic ring is however, preferably unsubstituted (i.e. n is zero).

Preferably $R^{18}$ is linear or branched, cyclic or acyclic, C1-20-alkyl, C2-C20 alkenyl, C2-C20 alkynyl, C6-C20-aryl, C7-C20-alkylaryl or C7-C20-arylalkyl radical, optionally containing one or more heteroatoms belonging to groups 14-16.

In some embodiments of the invention $R^{18}$ may represent a heteroaryl group, i.e. where a heteroatom or heteroatoms from groups 14-16 is present. Suitable heteroaryl groups include pyrrolyl, indolyl, furanyl, thiophenyl, oxazole, thiazole, isothiazole, isooxazole, triazole and pyridyl. It is preferred however if $R^{18}$ is free of heteroatoms.

More preferably $R^{18}$ is a linear or branched, $C_{1-10}$-alkyl radical. More preferably $R^{18}$ is a methyl or ethyl radical. It is within the scope of the invention for two $R^{18}$ groups to bind to the same atom of the ring although this is not preferred. Preferably the ring is unsubstituted.

$R^4$ is preferably a hydrogen atom or $C_{1-6}$ alkyl such as methyl, ethyl, propyl or isopropyl group, most preferably methyl or especially hydrogen.

W is preferably an optionally substituted phenyl group, or a 5 or 6 membered heteroaryl group such as a furanyl, thiophenyl, pyrrolyl, triazolyl, and pyridyl.

Any five membered heteroaryl group should preferably comprise one heteroatom in the ring, such as O, N or S.

Preferably W is a phenyl derivative. More preferably the phenyl derivative is unsubstituted or carries one substituent.

The optional substituent on any W group is $R^5$. If present, there should be 1 or 2 $R^5$ groups, preferably one $R^5$ group.

Preferably $R^5$ is a linear or branched, cyclic or acyclic, C1-C20-alkyl, C2-C20 alkenyl, C2-C20 alkynyl, C6-C20-aryl, C7-C20-alkylaryl or C7-C20-arylalkyl radical optionally containing one or more heteroatoms belonging to groups 14-16. Preferably $R^5$ is a linear or branched, cyclic or acyclic, C1-C10-alkyl group. Most preferably $R^5$ is a tert-butyl group.

It is preferred that any $R^5$ group present is located para to the bond to the indenyl group, i.e. at the 4-position of the ring.

In one preferred embodiment two adjacent $R^5$ groups taken together can form a further mono or multicyclic ring condensed to W. The new ring is preferably 5 or 6 membered or the $R^5$ groups preferably form two new rings such as one further five membered and six membered ring.

The new ring or rings can be aliphatic or aromatic. Preferably any new ring forms an aromatic system with the W ring to which it is attached.

In this way groups such as indolyl, carbazolyl, benzothiophenyl and naphthyl can be formed at position W. It is also within the scope of the invention for these new rings to be substituted by 1 or 2 $R^5$ groups (in which the option of two adjacent $R_5$ groups forming another ring is excluded).

In a most preferred embodiment, W is a phenyl group carrying one $R^5$ substituent. Preferably that substituent is carried para to the bond to the indenyl ring. That substituent is also preferably a $C_{1-10}$-alkyl radical. Furthermore, the carbon atom of the $R^5$ group bonding to the W ring is preferably a tertiary carbon atom.

Thus viewed from another aspect the invention provides a complex of formula (II):

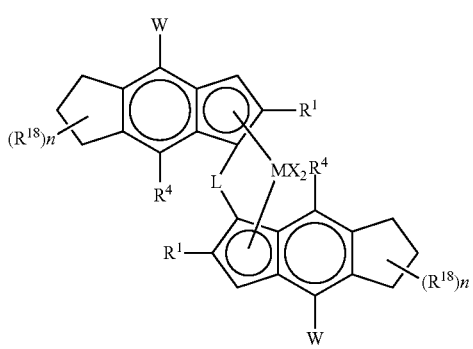

(II)

wherein

M is Zr or Hf;

each $R^1$ is $CH_2$-Ph, $CH_2$—$C(R^3)_{3-q}(H)_q$ wherein $R^3$ is a $C_{1-6}$-alkyl group or together two $R^3$ groups form a $C_{3-7}$-cycloalkyl ring wherein said ring is optionally substituted by a $C_{1-6}$ alkyl group and q can be 1 or 0;

L is ethylene or $SiR^6_2$;

$R^6$ is C1-10 alkyl, $C_{6-10}$-aryl, $C_{7-12}$-alkylaryl, or $C_{7-12}$-arylalkyl;

each X is a hydrogen atom, —OR, a halogen atom, or an R group;

R is $C_{1-10}$ alkyl each $R^4$ is H or $C_{1-3}$-alkyl;

n is 0 to 3;

each W' is aryl (e.g. phenyl), pyridyl, thiophenyl, or furyl optionally substituted by up to 2 groups $R^5$;

each $R^5$ is $C_{1-10}$-alkyl or two adjacent $R^5$ groups taken together form a phenyl ring fused to W' or two adjacent $R^5$ groups taken together form the atoms necessary to form a carbazolyl group with the W' group; and each $R^{18}$ is $C_{1-6}$-alkyl;

and wherein the two ligands forming the complex are identical.

In a preferred embodiment therefore the complex of the invention is of formula (III)

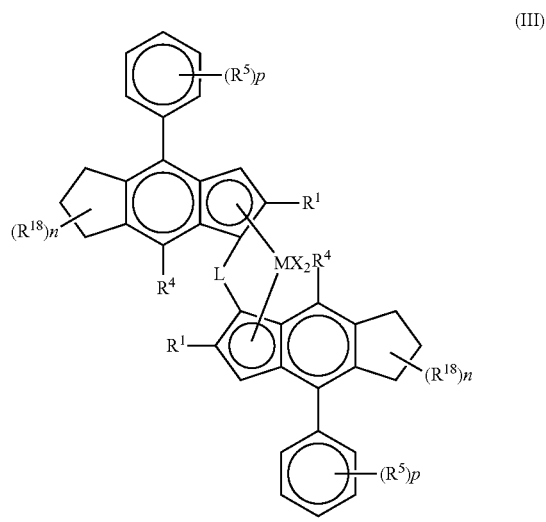

(III)

wherein

M is Zr or Hf;

each $R^1$ is $CH_2$-Ph, $CH_2$—$C(R^3)_{3-q}(H)_q$ wherein $R^3$ is a $C_{1-6}$-alkyl group or together two $R^3$ groups form a $C_{3-7}$-cycloalkyl ring wherein said ring is optionally substituted by a $C_{1-6}$ alkyl group and q can be 1 or 0;

L is $SiR^6_2$;

$R^6$ is C1-10 alkyl, $C_{6-10}$-aryl, $C_{7-12}$-alkylaryl, or $C_{7-12}$-arylalkyl;

each X is a hydrogen atom, OR, a halogen atom, or an R group;

R is $C_{1-10}$ alkyl each $R^4$ is H or $C_{1-3}$-alkyl;

n is 0 to 2;

p is 0 to 2;

each $R^5$ is $C_{1-10}$-alkyl and each $R^{18}$ is $C_{1-6}$-alkyl;

and wherein the two ligands forming the complex are identical.

In a still further preferred embodiment, the invention provides a complex of formula (IV)

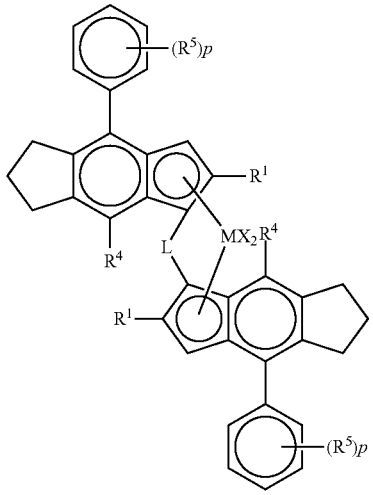

(IV)

in which:
M is Zr;
each $R^1$ is $CH_2$-Ph, $CH_2$—$C(R^3)_{3-q}(H)_q$ wherein $R^3$ is a $C_{1-6}$-alkyl group or together two $R^3$ groups form a $C_{3-7}$-cycloalkyl ring wherein said ring is optionally substituted by a $C_{1-6}$ alkyl group and q can be 1 or 0;
L is $SiR^6{}_2$;
$R^6$ is $C_{1-6}$ alkyl;
each X is a halogen atom, or methyl;
each $R^4$ is H or methyl
p is 0 or 1; and
$R^5$ is C1-6 alkyl;
and wherein the two ligands forming the complex are identical.

In a further highly preferred embodiment, the invention provides a complex of formula (V)

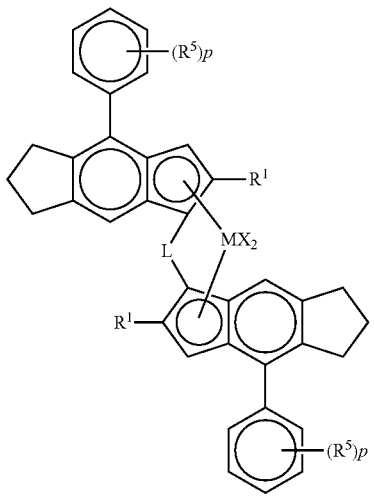

(V)

wherein p is 0 or 1;
L is $SiR^6{}_2$;
$R^5$ is a group $C(R^2)_3$;
$R^1$ is $CH_2$-Ph, $CH_2$—$C(R^3)_{3-q}(H)_q$ wherein $R^3$ is a $C_{1-6}$-alkyl group or together two $R^3$ groups form a $C_{3-7}$-cycloalkyl ring wherein said ring is optionally substituted by a $C_{1-6}$ alkyl group and q can be 1 or 0;

$R^2$ is a C1-6-alkyl group;
$R^3$ is a C1-6-alkyl group or together two $R^3$ groups form a $C_{3-7}$-cycloalkyl ring;
q is 0 or 1;
each X is a halogen atom, methoxy, or methyl; and
M is Zr;
and wherein the two ligands forming the complex are identical.

Some complexes of the invention are also new and form a further aspect of the invention. In particular, the invention provides a complex of formula (I), (II), (III), (IV) or (V) as herein before defined. Representatives of complexes of the above formulas include e.g. rac- and meso-1,1'-Dimethylsilylene-bis[2-isobutyl-4-(4-tert-butylphenyl)-5,6,7-trihydro-s-indacenyl]zirconium dichlorides, rac-1,1'-dimethylsililene-bis[2-(cyclohexylmethyl)-4-(4-tert-butylphenyl)-5,6,7-trihydro-s-indacen-1-yl]zirconium dichloride, rac-1,1'-dimethylsililene-bis[2-(2,2,-dimethylpropyl)-4-(4-tert-butylphenyl)-5,6,7-trihydro-s-indacen-1-yl]zirconium dichloride and rac-1,1'-dimethylsililene-bis[2-benzyl-4-(4-tert-butylphenyl)-5,6,7-trihydro-s-indacen-1-yl]zirconium dichloride. Especially preferred complexes are rac- and meso-1,1'-dimethylsilylene-bis[2-isobutyl-4-(4-tert-butylphenyl)-5,6,7-trihydro-s-indacenyl]zirconium dichlorides and rac-1,1'-dimethylsililene-bis[2-(cyclohexylmethyl)-4-(4-tert-butylphenyl)-5,6,7-trihydro-s-indacen-1-yl]zirconium dichloride.

Furthermore, it is submitted that ligands of formula (I) to (V) are also new and form a further aspect of the invention. The ligands do not contain the $MX_2$ group and the Cp ring contains a double bond. Thus, a ligand of formula (II) is represented by the formula:

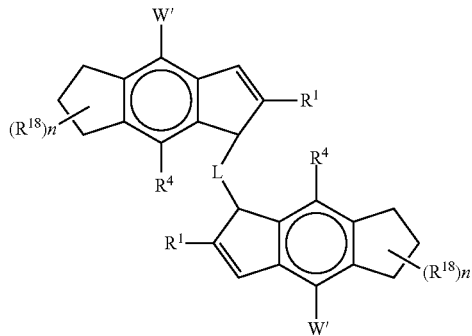

For the avoidance of doubt, any narrower definition of a substituent offered above can be combined with any other broad or narrowed definition of any other substituent.

Throughout the disclosure above, where a narrower or preferred definition of a substituent is presented, that narrower or preferred definition is deemed disclosed in conjunction with all broader and narrower and preferred definitions of other substituents in the application.

Synthesis

The ligands required to form the catalysts of the invention can be synthesised by any process and the skilled organic chemist would be able to devise various synthetic protocols for the manufacture of the necessary ligand materials. WO2006/097497 and the other prior art references mentioned above disclose the necessary chemistry and as herein incorporated by reference. Moreover, our examples set out a synthesis in which the tricyclic ring structure which forms the basis of the metallocenes of the invention is manufactured through the combination of indane and 2-isobutylacrylic acid.

It will be appreciated that by manipulating the nature of the acid, different $R_1$ groups can be prepared.

The process starts with indane acylation and subsequent cyclisation of the reaction product, followed by one pot aldol condensation and hydrogenation of the α.β-unsaturated ketone to give the desired 2-(substituted)-3,5,6,7-tetrahydro-s-indacen-1(2H)-one. In brief, we form an unsubstituted indacen-1-one which we then alkylate in the 2 position by aldol condensation with the desired $R_1$ carbaldehyde.

The rest of the synthesis is conventional and the synthetic protocols described in the examples will be readily adapted by the skilled man to allow the synthesis of a wide range of complexes.

The new synthetic protocols form a still yet further aspect of the invention. Thus viewed from another aspect the invention provides a process for the preparation of a compound of formula (VI)

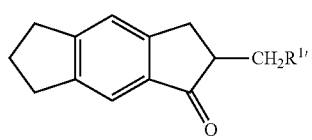

(VI)

comprising reacting a compound of formula (VII)

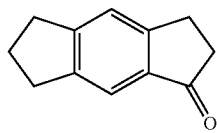

(VII)

with the compound $R^{1'}$CHO and hydrogenating the reaction product;
wherein $R^{1'}$ is as hereinbefore defined.

It is also possible to synthesize a compound of formula (VIII)

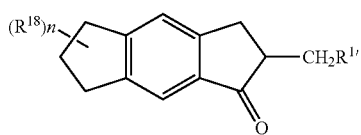

(VIII)

where $R^{18}$ and n are as hereinbefore defined using the same chemistry in which the $R^{18}$ group is present in the starting material.

The starting material can be prepared by an acylation reaction involving a ring formation reaction as shown below.

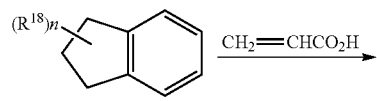

-continued

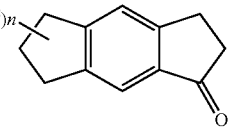

The use of $P_4O_{10}$ and methanesulfonic acid is preferred to ensure this reaction completes.

Cocatalyst

To form an active catalytic species it is normally necessary to employ a cocatalyst as is well known in the art. Cocatalysts comprising an organometallic compound of Group 13 metal, like organoaluminium compounds used to activate metallocene catalysts are suitable for use in this invention.

The olefin polymerisation catalyst system of the invention comprises (i) a complex in which the metal ion is coordinated by a ligand of the invention; and normally (ii) an aluminium alkyl compound (or other appropriate cocatalyst), or the reaction product thereof. Thus the cocatalyst is preferably an alumoxane, like MAO or an alumoxane other than MAO.

Alternatively, however, the catalysts of the invention may be used with other cocatalysts, e.g. boron compounds such as $B(C_6F_5)_3$, $C_6H_5N(CH_3)_2H:B(C_6F_5)_4$, $(C_6H_5)_3C:B(C_6F_5)_4$ or $Ni(CN)_4[B(C_6F_5)_3]_4{}^{2-}$.

The use of aluminoxanes, especially MAO, is highly preferred.

Suitable amounts of cocatalyst will be well known to the skilled man. Typically Al to M molar ratios are from 1:1 to 1000:1 mol/mol. Preferably when an aluminium alkyl is used as a coctalyst, the molar ratio of the aluminium in the activator to the transition metal in the complex is from 1 to 500 mol/mol, preferably from 10 to 400 mol/mol and in particular from 50 to 400 mol/mol.

Manufacture

The metallocene complex of the present invention can be used in combination with a suitable cocatalyst as a catalyst for the polymerization of olefins, e.g. in a solvent such as toluene or an aliphatic hydrocarbon, (i.e. for polymerization in solution), as it is well known in the art. Preferably, polymerization of olefins, especially propylene, takes place in the condensed phase or in gas phase.

The catalyst of the invention is preferably in solid particulate form, e.g. as obtained for example by supporting on an inert organic or inorganic carrier, such as for example silica or in solid particulate form but unsupported.

The particulate support material used is preferably an organic or inorganic material, such as silica, alumina or zirconia or a mixed oxide such as silica-alumina, in particular silica, alumina or silica-alumina.

Especially preferably the support is a porous material so that the complex may be loaded into the pores of the support, e.g. using a process analogous to those described in WO94/14856 (Mobil), WO95/12622 (Borealis) and WO2006/097497. The particle size is not critical but is preferably in the range 5 to 200 μm, more preferably 40 to 100 μm. The use of these supports is routine in the art.

In one particular embodiment, no external carrier is used. In order to provide the catalyst of the invention in solid form but without using an external carrier, it is preferred if a liquid liquid emulsion system is used. The process involves forming dispersing catalyst components (i) and (ii) in a solvent, and solidifying said dispersed droplets to form solid particles.

In particular, the method involves preparing a solution of one or more catalyst components; dispersing said solution in an solvent to form an emulsion in which said one or more catalyst components are present in the droplets of the dispersed phase; immobilising the catalyst components in the dispersed droplets, in the absence of an external particulate porous support, to form solid particles comprising the said catalyst, and optionally recovering said particles.

This process enables the manufacture of active catalyst particles with improved morphology, e.g. with a predetermined spherical shape and particle size and without using any added external porous support material, such as an inorganic oxide, e.g. silica. Also desirable surface properties can be obtained.

By the term "preparing a solution of one or more catalyst components" is meant that the catalyst forming compounds may be combined in one solution which is dispersed to the immiscible solvent, or, alternatively, at least two separate catalyst solutions for each part of the catalyst forming compounds may be prepared, which are then dispersed successively to the solvent.

In a preferred method for forming the catalyst at least two separate solutions for each or part of said catalyst may be prepared, which are then dispersed successively to the immiscible solvent.

More preferably, a solution of the complex comprising the transition metal compound and the cocatalyst is combined with the solvent to form an emulsion wherein that inert solvent forms the continuous liquid phase and the solution comprising the catalyst components forms the dispersed phase (discontinuous phase) in the form of dispersed droplets. The droplets are then solidified to form solid catalyst particles, and the solid particles are separated from the liquid and optionally washed and/or dried. The solvent forming the continuous phase may be immiscible to the catalyst solution at least at the conditions (e.g. temperatures) used during the dispersing step.

The term "immiscible with the catalyst solution" means that the solvent (continuous phase) is fully immiscible or partly immiscible i.e. not fully miscible with the dispersed phase solution.

Preferably said solvent is inert in relation to the compounds of the catalyst system to be produced. Full disclosure of the necessary process can be found in WO03/051934 which is herein incorporated by reference.

The inert solvent must be chemically inert at least at the conditions (e.g. temperature) used during the dispersing step. Preferably, the solvent of said continuous phase does not contain dissolved therein any significant amounts of catalyst forming compounds. Thus, the solid particles of the catalyst are formed in the droplets from the compounds which originate from the dispersed phase (i.e. are provided to the emulsion in a solution dispersed into the continuous phase).

The terms "immobilisation" and "solidification" are used herein interchangeably for the same purpose, i.e. for forming free flowing solid catalyst particles in the absence of an external porous particulate carrier, such as silica. The solidification happens thus within the droplets. Said step can be effected in various ways as disclosed in said WO03/051934 Preferably solidification is caused by an external stimulus to the emulsion system such as a temperature change to cause the solidification. Thus in said step the catalyst component (s) remain "fixed" within the formed solid particles. It is also possible that one or more of the catalyst components may take part in the solidification/immobilisation reaction.

Accordingly, solid, compositionally uniform particles having a predetermined particle size range can be obtained.

Furthermore, the particle size of the catalyst particles of the invention can be controlled by the size of the droplets in the solution, and spherical particles with a uniform particle size distribution can be obtained.

The invention is also industrially advantageous, since it enables the preparation of the solid particles to be carried out as a one-pot procedure. Continuous or semicontinuous processes are also possible for producing the catalyst.

Dispersed Phase

The principles for preparing two phase emulsion systems are known in the chemical field. Thus, in order to form the two phase liquid system, the solution of the catalyst component (s) and the solvent used as the continuous liquid phase have to be essentially immiscible at least during the dispersing step. This can be achieved in a known manner e.g. by choosing said two liquids and/or the temperature of the dispersing step/solidifying step accordingly.

A solvent may be employed to form the solution of the catalyst component (s). Said solvent is chosen so that it dissolves said catalyst component (s). The solvent can be preferably an organic solvent such as used in the field, comprising an optionally substituted hydrocarbon such as linear or branched aliphatic, alicyclic or aromatic hydrocarbon, such as a linear or cyclic alkane, an aromatic hydrocarbon and/or a halogen containing hydrocarbon.

Examples of aromatic hydrocarbons are toluene, benzene, ethylbenzene, propylbenzene, butylbenzene and xylene. Toluene is a preferred solvent. The solution may comprise one or more solvents. Such a solvent can thus be used to facilitate the emulsion formation, and usually does not form part of the solidified particles, but e.g. is removed after the solidification step together with the continuous phase.

Alternatively, a solvent may take part in the solidification, e.g. an inert hydrocarbon having a high melting point (waxes), such as above 40° C., suitably above 70° C., e.g. above 80° C. or 90° C., may be used as solvents of the dispersed phase to immobilise the catalyst compounds within the formed droplets.

In another embodiment, the solvent consists partly or completely of a liquid monomer, e.g. liquid olefin monomer designed to be polymerised in a "prepolymerisation" immobilisation step.

Continuous Phase

The solvent used to form the continuous liquid phase is a single solvent or a mixture of different solvents and may be immiscible with the solution of the catalyst components at least at the conditions (e.g. temperatures) used during the dispersing step. Preferably said solvent is inert in relation to said compounds.

The term "inert in relation to said compounds" means herein that the solvent of the continuous phase is chemically inert, i.e. undergoes no chemical reaction with any catalyst forming component. Thus, the solid particles of the catalyst are formed in the droplets from the compounds which originate from the dispersed phase, i.e. are provided to the emulsion in a solution dispersed into the continuous phase.

It is preferred that the catalyst components used for forming the solid catalyst will not be soluble in the solvent of the continuous liquid phase. Preferably, said catalyst components are essentially insoluble in said continuous phase forming solvent.

Solidification takes place essentially after the droplets are formed, i.e. the solidification is effected within the droplets e.g. by causing a solidifying reaction among the compounds present in the droplets. Furthermore, even if some solidifying agent is added to the system separately, it reacts within the droplet phase and no catalyst forming components go into the continuous phase.

The term "emulsion" used herein covers both bi- and multiphasic systems.

In a preferred embodiment said solvent forming the continuous phase is an inert solvent including a halogenated organic solvent or mixtures thereof, preferably fluorinated organic solvents and particularly semi, highly or perfluorinated organic solvents and functionalised derivatives thereof. Examples of the above-mentioned solvents are semi, highly or perfluorinated hydrocarbons, such as alkanes, alkenes and cycloalkanes, ethers, e.g. perfluorinated ethers and amines, particularly tertiary amines, and functionalised derivatives thereof. Preferred are semi, highly or perfluorinated, particularly perfluorinated hydrocarbons, e.g. perfluorohydrocarbons of e.g. C3-C30, such as C4-C10. Specific examples of suitable perfluoroalkanes and perfluorocycloalkanes include perfluoro-hexane, -heptane, -octane and -(methylcyclohexane). Semi fluorinated hydrocarbons relates particularly to semifluorinated n-alkanes, such as perfluoroalkyl-alkane.

"Semi fluorinated" hydrocarbons also include such hydrocarbons wherein blocks of —C—F and —C—H alternate. "Highly fluorinated" means that the majority of the —C—H units are replaced with —C—F units. "Perfluorinated" means that all —C—H units are replaced with —C—F units. See the articles of A. Enders and G. Maas in "Chemie in unserer Zeit", 34. Jahrg. 2000, Nr. 6, and of Pierandrea Lo Nostro in "Advances in Colloid and Interface Science", 56 (1995) 245-287, Elsevier Science.

Dispersing Step

The emulsion can be formed by any means known in the art: by mixing, such as by stirring said solution vigorously to said solvent forming the continuous phase or by means of mixing mills, or by means of ultra sonic wave, or by using a so called phase change method for preparing the emulsion by first forming a homogeneous system which is then transferred by changing the temperature of the system to a biphasic system so that droplets will be formed.

The two phase state is maintained during the emulsion formation step and the solidification step, as, for example, by appropriate stirring.

Additionally, emulsifying agents/emulsion stabilisers can be used, preferably in a manner known in the art, for facilitating the formation and/or stability of the emulsion. For the said purposes e.g. surfactants, e.g. a class based on hydrocarbons (including polymeric hydrocarbons with a molecular weight e.g. up to 10 000 and optionally interrupted with a heteroatom(s)), preferably halogenated hydrocarbons, such as semi- or highly fluorinated hydrocarbons optionally having a functional group selected e.g. from —OH, —SH, NH$_2$, NR"$_2$. —COOH, —COONH$_2$, oxides of alkenes, —CR"=CH$_2$, where R" is hydrogen, or C1-C20 alkyl, C2-20-alkenyl or C2-20-alkynyl group, oxo-groups, cyclic ethers and/or any reactive derivative of these groups, like alkoxy, or carboxylic acid alkyl ester groups, or, preferably semi-, highly- or perfluorinated hydrocarbons having a functionalised terminal, can be used. The surfactants can be added to the catalyst solution, which forms the dispersed phase of the emulsion, to facilitate the forming of the emulsion and to stabilize the emulsion.

Alternatively, an emulsifying and/or emulsion stabilising aid can also be formed by reacting a surfactant precursor bearing at least one functional group with a compound reactive with said functional group and present in the catalyst solution or in the solvent forming the continuous phase. The obtained reaction product acts as the actual emulsifying aid and or stabiliser in the formed emulsion system.

Examples of the surfactant precursors usable for forming said reaction product include e.g. known surfactants which bear at least one functional group selected e.g. from —OH, —SH, NH$_2$, NR"$_2$. —COOH, —COONH$_2$, oxides of alkenes, —CR"=CH$_2$, where R" is hydrogen, or C1-C20 alkyl, C2-20-alkenyl or C2-20-alkynyl group, oxo-groups, cyclic ethers with 3 to 5 ring atoms, and/or any reactive derivative of these groups, like alkoxy or carboxylic acid alkyl ester groups; e.g. semi-, highly or perfluorinated hydrocarbons bearing one or more of said functional groups. Preferably, the surfactant precursor has a terminal functionality as defined above.

The compound reacting with such surfactant precursor is preferably contained in the catalyst solution and may be a further additive or one or more of the catalyst forming compounds. Such compound is e.g. a compound of group 13 (e.g. MAO and/or an aluminium alkyl compound and/or a transition metal compound).

If a surfactant precursor is used, it is preferably first reacted with a compound of the catalyst solution before the addition of the transition metal compound. In one embodiment e.g. a highly fluorinated C1-n (suitably C4-30- or C5-15) alcohol (e.g. highly fluorinated heptanol, octanol or nonanol), oxide (e.g. propenoxide) or acrylate ester is reacted with a cocatalyst to form the "actual" surfactant. Then, an additional amount of cocatalyst and the transition metal compound is added to said solution and the obtained solution is dispersed to the solvent forming the continuous phase. The "actual" surfactant solution may be prepared before the dispersing step or in the dispersed system. If said solution is made before the dispersing step, then the prepared "actual" surfactant solution and the transition metal solution may be dispersed successively (e.g. the surfactant solution first) to the immiscible solvent, or be combined together before the dispersing step.

Solidification

The solidification of the catalyst component(s) in the dispersed droplets can be effected in various ways, e.g. by causing or accelerating the formation of said solid catalyst forming reaction products of the compounds present in the droplets. This can be effected, depending on the used compounds and/or the desired solidification rate, with or without an external stimulus, such as a temperature change of the system.

In a particularly preferred embodiment, the solidification is effected after the emulsion system is formed by subjecting the system to an external stimulus, such as a temperature change. Temperature differences of e.g. 5 to 100° C., such as 10 to 100° C., or 20 to 90° C., such as 50 to 90° C.

The emulsion system may be subjected to a rapid temperature change to cause a fast solidification in the dispersed system. The dispersed phase may e.g. be subjected to an immediate (within milliseconds to few seconds) temperature change in order to achieve an instant solidification of the component (s) within the droplets. The appropriate temperature change, i.e. an increase or a decrease in the temperature of an emulsion system, required for the desired solidification rate of the components cannot be limited to any specific range, but naturally depends on the emulsion system, i. a. on the used compounds and the concentrations/ratios thereof, as well as on the used solvents, and is chosen accordingly. It is also evident that any techniques may be used to provide sufficient heating or cooling effect to the dispersed system to cause the desired solidification.

In one embodiment the heating or cooling effect is obtained by bringing the emulsion system with a certain temperature to an inert receiving medium with significantly different temperature, e.g. as stated above, whereby said temperature change of the emulsion system is sufficient to cause the rapid solidification of the droplets. The receiving medium can be gaseous, e.g. air, or a liquid, preferably a solvent, or a mixture of two or more solvents, wherein the catalyst component(s) is (are) immiscible and which is inert in relation to the catalyst component(s). For instance, the receiving medium comprises the same immiscible solvent used as the continuous phase in the first emulsion formation step.

Said solvents can be used alone or as a mixture with other solvents, such as aliphatic or aromatic hydrocarbons, such as alkanes. Preferably a fluorinated solvent as the receiving medium is used, which may be the same as the continuous phase in the emulsion formation, e.g. perfluorinated hydrocarbon.

Alternatively, the temperature difference may be effected by gradual heating of the emulsion system, e.g. up to 10° C. per minute, preferably 0.5 to 6° C. per minute and more preferably in 1 to 5° C. per minute.

In case a melt of e.g. a hydrocarbon solvent is used for forming the dispersed phase, the solidifcation of the droplets may be effected by cooling the system using the temperature difference stated above.

Preferably, the "one phase" change as usable for forming an emulsion can also be utilised for solidifying the catalytically active contents within the droplets of an emulsion system by, again, effecting a temperature change in the dispersed system, whereby the solvent used in the droplets becomes miscible with the continuous phase, preferably a fluorous continuous phase as defined above, so that the droplets become impoverished of the solvent and the solidifying components remaining in the "droplets" start to solidify. Thus the immisciblity can be adjusted with respect to the solvents and conditions (temperature) to control the solidification step.

The miscibility of e.g. organic solvents with fluorous solvents can be found from the literature and be chosen accordingly by a skilled person. Also the critical temperatures needed for the phase change are available from the literature or can be determined using methods known in the art, e.g. the Hildebrand-Scatchard-Theorie. Reference is also made to the articles of A. Enders and G. and of Pierandrea Lo Nostro cited above.

Thus according to the invention, the entire or only part of the droplet may be converted to a solid form. The size of the "solidified" droplet may be smaller or greater than that of the original droplet, e.g. if the amount of the monomer used for the prepolymerisation is relatively large.

The solid catalyst particles recovered can be used, after an optional washing step, in a polymerisation process of an olefin. Alternatively, the separated and optionally washed solid particles can be dried to remove any solvent present in the particles before use in the polymerisation step. The separation and optional washing steps can be effected in a known manner, e.g. by filtration and subsequent washing of the solids with a suitable solvent.

The droplet shape of the particles may be substantially maintained. The formed particles may have an average size range of 1 to 500 μm, e.g. 5 to 500 μm, advantageously 5 to 200 μm or 10 to 150 μm. Even an average size range of 5 to 60 μm is possible. The size may be chosen depending on the polymerisation the catalyst is used for. Advantageously, the particles are essentially spherical in shape, they have a low porosity and a low surface area.

The formation of solution can be effected at a temperature of 0-100° C., e.g. at 20-80° C. The dispersion step may be effected at −20° C.-100° C., e.g. at about −10-70° C., such as at −5 to 30° C., e.g. around 0° C.

To the obtained dispersion an emulsifying agent as defined above, may be added to improve/stabilise the droplet formation. The solidification of the catalyst component in the droplets is preferably effected by raising the temperature of the mixture, e.g. from 0° C. temperature up to 100° C., e.g. up to 60-90° C., gradually. E.g. in 1 to 180 minutes, e.g. 1-90 or 5-30 minutes, or as a rapid heat change. Heating time is dependent on the size of the reactor.

During the solidification step, which is preferably carried out at about 60 to 100° C., preferably at about 75 to 95° C., (below the boiling point of the solvents) the solvents may preferably be removed and optionally the solids are washed with a wash solution, which can be any solvent or mixture of solvents such as those defined above and/or used in the art, preferably a hydrocarbon, such as pentane, hexane or heptane, suitably heptane. The washed catalyst can be dried or it can be slurried into an oil and used as a catalyst-oil slurry in polymerisation process.

All or part of the preparation steps can be done in a continuous manner. Reference is made to WO2006/069733 describing principles of such a continuous or semicontinuous preparation methods of the solid catalyst types, prepared via emulsion/solidification method.

Polymerisation

The olefin polymerized using the catalyst of the invention is preferably propylene or a higher alpha-olefin or a mixture of ethylene and an α-olefin or a mixture of alpha olefins, for example $C_{2-20}$ olefins, e.g. ethylene, propylene, 1-butene, 1-hexene, 4-methyl-1-pentene, 1-octene etc. The olefins polymerized in the method of the invention may include any compound which includes unsaturated polymerizable groups. Thus, for example unsaturated compounds, such as $C_{6-20}$ olefins (including cyclic and polycyclic olefins (e.g. norbornene)), and polyenes, especially $C_{4-20}$ dienes, may be included in a comonomer mixture with lower olefins, e.g. $C_{2-5}$ α-olefins. Diolefins (i.e. dienes) are suitably used for introducing long chain branching into the resultant polymer. Examples of such dienes include α,ωlinear dienes such as 1,5-hexadiene, 1,6-heptadiene, 1,8-nonadiene, 1,9-decadiene, etc.

The catalysts of the present invention are particularly suited for use in the manufacture of polypropylene polymers.

Polymerization in the method of the invention may be effected in one or more, e.g. 1, 2 or 3, polymerization reactors, using conventional polymerization techniques, e.g. gas phase, solution phase, slurry or bulk polymerization.

In general, a combination of slurry (or bulk) and at least one gas phase reactor is often preferred, particularly with the reactor order being slurry (or bulk) then one or more gas phase reactors.

In case of propylene polymerisation for slurry reactors, the reaction temperature will generally be in the range 60 to 110° C. (e.g. 60-90° C.), the reactor pressure will generally be in the range 5 to 80 bar (e.g. 20-60 bar), and the residence time will generally be in the range 0.1 to 5 hours (e.g. 0.3 to 2 hours). The monomer is usually used as reaction medium.

For gas phase reactors, the reaction temperature used will generally be in the range 60 to 115° C. (e.g. 70 to 110° C.), the reactor pressure will generally be in the range 10 to 25 bar, and the residence time will generally be 0.5 to 8 hours (e.g. 0.5 to 4 hours) The gas used will be the monomer optionally as mixture with a non-reactive gas such as nitrogen or propane. In addition to actual polymerisation steps and reactors, the process can contain any additional polymerisation steps, like prepolymerisation step, and any further after reactor handling steps as known in the art.

Generally the quantity of catalyst used will depend upon the nature of the catalyst, the reactor types and conditions and the properties desired for the polymer product. As is well known in the art hydrogen can be used for controlling the molecular weight of the polymer. It is particularly notable that the catalyst of the present invention performs exceptionally well over a wide range of hydrogen concentration used during the polymerisation process, which makes the catalyst beneficial to be used for productions of a wide range of polymers This forms a further aspect of the invention. The catalysts are useful at higher hydrogen concentrations as well with lower hydrogen concentrations to get polymer with higher molecular weight. The activity of the catalysts of the invention is also very high and the polymer productivity levels are excellent.

The propylene polymers made using the catalysts of the invention form a still yet further aspect of the invention. The catalysts of the invention enable the formation of high molecular weight, low xylene soluble polymers which also possess high isotacticity. Isotacticity is measured by $^{13}$C NMR or also by DSC. Thus, in the case of polypropylene homopolymers, isotacticity can be higher than 90% mm, preferably higher than 95% mm, even more preferably higher than 99.5% mm when measured by $^{13}$C NMR. When measured by standard DSC, the high isotacticity of the polypropylene homopolymers means a melting point (Tm) higher than 150° C., preferably higher than 152° C., even more preferably higher than 155° C.

The molecular weight of the polypropylene can be at least 300,000, preferably at least 400,000, especially at least 500,000. However, the molecular weight of the formed polymer is dependent on the amount of hydrogen employed, as is well known in the art.

Preferably, xylene soluble content of the polymer made by the catalyst of the invention is less than 1 wt %, more preferably less than 0.5 wt %, even more preferably less than 0.35 wt %.

The polymers made by the catalysts of the invention are useful in all kinds of end articles such as pipes, films (cast, blown and BOPP films), fibers, moulded articles (e.g. injection moulded, blow moulded, rotomoulded articles), extrusion coatings and so on. Film applications, such as those requiring BOPP (bi-oriented polypropylene) film, especially for capacitors are favoured.

The invention will now be illustrated by reference to the following non-limiting Examples.

Measurement Methods:

Al and Zr Determination (ICP-Method)

The elementary analysis of a catalyst was performed by taking a solid sample of mass, M, cooling over dry ice. Samples were diluted up to a known volume, V, by dissolving in nitric acid (HNO$_3$, 65%, 5% of V) and freshly deionised (DI) water (5% of V). The solution was then added to hydrofluoric acid (HF, 40%, 3% of V), diluted with DI water up to the final volume, V, and left to stabilise for two hours. The analysis was run at room temperature using a Thermo Elemental IRIS Advantage XUV Inductively Coupled Plasma-Atomic Excitation Spectrometer (ICP-AES) which was calibrated immediately before analysis using a blank (a solution of 5% HNO$_3$, 3% HF in DI water), a low standard (10 ppm Al in a solution of 5% HNO$_3$, 3% HF in DI water), a high standard (50 ppm Al, 20 ppm Zr in a solution of 5% HNO$_3$, 3% HF in DI water) and a quality control sample (20 ppm Al, 10 ppm Zr in a solution of 5% HNO$_3$, 3% HF in DI water). The content of zirconium was monitored using the 339.198 nm line, the content of aluminium via the 396.152 nm line and the potassium using the 766.490 nm line. The reported values, required to be between 0 and 100, or further dilution is required, are an average of three successive aliquots taken from the same sample and are related back to the original catalyst using equation 1.

$$C = \frac{R \times V}{M} \quad \text{Equation 1}$$

Where:
C is the concentration in ppm, related to % content by a factor of 10,000
R is the reported value from the ICP-AES
V is the total volume of dilution in ml
M is the original mass of sample in g If dilution was required then this also needs to be taken into account by multiplication of C by the dilution factor.

Intrinsic Viscosity

Polymer samples were dissolved in decalin at the concentration of 1 mg/ml and at the temperature of 135° C. The relative viscosity of the dilute polymer solution was measured according to the ISO1628-1 by use of an Automated Ubbelohde Capillary Viscometer; LAUDA PVS1. The relative viscosity of the dissolved polymer solution was determined as a ratio of the measured kinematic viscosities of the polymer solution and the pure solvent. Intrinsic viscosity was calculated from a single viscosity measurement at known concentration by use of Huggins equation and known Huggins constant.

Melting Temperature $T_m$ [° C.] and Crystallisation Temperature $T_c$ [° C.]:

Melting temperature ($T_m$), crystallization temperature ($T_c$), were measured (according to ISO 11357-3:1999) with Mettler TA820 differential scanning calorimetry (DSC) on 5 to 10 mg, typically 8±0.5 mg samples. Both crystallization and melting curves were obtained during 10° C./min cooling and heating scans between 30° C. and 225° C. Melting and crystallization temperatures were taken as the peaks of endotherms and exotherms. The peak temperature of the second heating scan was taken as the melting temperature.

Melt Flow Rate

The melt flow rate (MFR) is determined according to ISO 1133 and is indicated in g/10 min. The MFR is an indication of the flowability, and hence the processability, of the polymer. The higher the melt flow rate, the lower the viscosity of the polymer. The MFR is determined at 230° C. and may be determined at different loadings such as 2.16 kg (MFR$_2$) or 21.6 kg (MFR$_{21}$).

GPC: Molecular Weight Averages, Molecular Weight Distribution, and Polydispersity Index (Mn, Mw, MWD)

Molecular weight averages (Mw, Mn), Molecular weight distribution (MWD) and its broadness, described by polydispersity index, PDI=Mw/Mn (wherein Mn is the number average molecular weight and Mw is the weight average molecular weight) were determined by Gel Permeation Chromatography (GPC) according to ISO 16014-4:2003 and ASTM D 6474-99. A Waters GPCV2000 instrument, equipped with differential refractive index detector and online viscosimeter was used with 2×GMHXL-HT and 1×G7000HXL-HT TSK-gel columns from Tosoh Bioscience and 1,2,4-trichlorobenzene (TCB, stabilized with 250 mg/L 2,6-Di tert butyl-4-methyl-phenol) as solvent at 140° C. and at a constant flow rate of 1 mL/min. 209.5 µL of sample solution were injected per analysis. The column set was calibrated using universal calibration (according to ISO 16014-2:2003) with at least 15 narrow MWD polystyrene (PS) standards in the range of 1 kg/mol to 12 000 kg/mol. Mark Houwink constants for PS, PE and PP used are as per ASTM D 6474-99. All samples were prepared by dissolving 0.5-4.0 mg of polymer in 4 mL (at 140° C.) of stabilized TCB (same as mobile phase) and keeping for max. 3 hours at max. 160° C. with continuous gentle shaking prior sampling into the GPC instrument.

Xylene Solubles 2.0 g of polymer is dissolved in 250 ml p-xylene at 135° C. under agitation. After 30 minutes the solution is allowed to cool for 15 minutes at ambient temperature and then allowed to settle for 30 minutes at 25° C. The solution is filtered with filter paper into two 100 ml flasks. The solution from the first 100 ml vessel is evaporated in nitrogen flow and the residue is dried under vacuum at 90° C. until constant weight is reached.

$$XS\% = (100 \cdot m \cdot V_0)/(m_0 \cdot v);$$

$m_0$=initial polymer amount (g); m=weight of residue (g); $V_0$=initial volume (ml); v=volume of analysed sample (ml).

Catalyst Activity

The catalyst activity was calculated on the basis of following formula:

$$\text{Catalyst Activity (kg/g*h)} = \frac{\text{amount of polymer produced (kg)}}{\text{catalyst loading (g)} \times \text{polymerisation time (h)}}$$

$^{13}$C NMR

Quantitative solution state $^{13}$C {$^{1}$H} nuclear magnetic resonance (NMR) spectra were recorded using a Bruker Avance III 400 NMR spectrometer with a 9.4 T superconducting standard-bore magnet operating at 400.15 and 100.62 MHz for $^{1}$H and $^{13}$C respectively. Approximately 200 mg of material and 0.5 mg of stabiliser (e.g. BHT) were dissolved in approximately 3 ml of 1,1,2,2-tetrachloroethane-d$_2$ (TCE-d$_2$) inside a 10 mm NMR tube. The measurements were done at 125° C. using a $^{13}$C optimised 10 mm selective excitation probehead with nitrogen gas for all pneumatics. The data was acquired with standard 90° single-pulse excitation with NOE and bi-level WALTZ16 decoupling scheme. A total of 6144 (6 k) transients were acquired per spectra using a recycle delay of 3 seconds and an acquisition time of 1.6 seconds.

The tacticity distribution at the pentad level and regioerrors were determined from the quantitative $^{13}$C {$^{1}$H} NMR spectra after basic assignment as in: V. Busico and R. Cipullo, *Progress in Polymer Science*, 2001, 26, 443-533, and based on the method described in: C. De Rosa, F. Auriemma, M. Paolillo, L. Resconi, I. Camurati, *Macromolecules* 2005, 38(22), 9143-9154. Quantification of the pentad distribution was done through integration of the methyl region in the $^{13}$C {$^{1}$H} spectra and when applicable corrected for any sites not related to the stereo sequences of interest, e.g. regio misinsertions.

The amount of misinsertions of propylene monomers in the chain was determined by $^{13}$C {$^{1}$H} NMR spectroscopy. The amount of 2,1 erythro misinsertions was calculated using the arithmetic average of the integrated areas from 17.0-17.4 ppm and 17.4-17.8 ppm divided by the sum of integrated areas of all the CH$_3$ signals. The amount of 2,1 threo misinsertions was calculated using the arithmetic average of the integrated areas from 14.55-14.05 ppm and 15.05-15.55 ppm divided by the sum of integrated areas of all the CH$_3$ signals. The amount of 3,1 misinsertions was calculated using half of the arithmetic average of the integrated areas from 27.25-27.85 ppm and 37.15-37.75 ppm divided by the sum of integrated areas of all the CH$_3$ signals.

EXAMPLES

General Procedures and Starting Materials

All manipulations with air and moisture sensitive compounds were performed either in an atmosphere of thoroughly purified argon using a standard Schlenk technique or in a controlled atmosphere Glove Box (Mecaplex, VAC or M. Braun). Tetrahydrofurane (Merck) and diethyl ether (Merck) for synthesis were purified by distillation over LiAlH$_4$ and kept over sodium benzophenone ketyl. Toluene (Merck) and hexanes (Merck) were distilled and stored over CaH$_2$ or Na/K alloy. Dichloromethane (Merck) for organometallic synthesis as well as CD$_2$Cl$_2$ (Merck) were distilled and stored over CaH$_2$. Chloroform-d (Merck) was distilled over P$_4$O$_{10}$ and stored over molecular sheves (3 Å). Methanol (Merck), dimethylformamide (Merck), dichloromethane (Merck), ethyl acetoacetate (Acros), isobutylbromide (Merck), bis(trimethylsilyl)amine (Merck), para-toluenesulfonic acid (Aldrich), paraformaldehyde (Merck), methanesulfonic acid (Aldrich), ZrCl$_4$(THF)$_2$ (Aldrich), CuBr (Acros), 2.5 M $^n$BuLi in hexanes (Chemetall), Pd(dba)$_2$ (Aldrich), NaBH$_4$ (Acros), dicyclohexyl(2',6'-dimethoxybiphenyl-2-yl)phosphine (Aldrich), 60% suspension of NaH in mineral oil (Aldrich), 4-tert-butylphenylboronic acid (Aldrich), anhydrous powdered AlCl$_3$ (Merck), dichlorodimethylsilane (Merck), K$_3$PO$_4$ (Fluka), P$_4$O$_{10}$ (Merck), Cyclohexanecarbaldehyde (Aldrich), 10% Pd on charcoal (Aldrich), hydrogen gas (Linde), KOH (Merck), Na$_2$SO$_4$ (Akzo Nobel), TsOH (Aldrich), 12 M HCl (Reachim, Russia), 96% ethanol (Merck), Silica Gel 60 40-63 µm (Merck) were used as obtained. Celite 503 (Aldrich) was dried in vacuum at 200° C. before use. 3,5,6,7-Tetrahydro-s-indacen-1(2H)-one was synthesized via acylation of indan (ABCR) by 3-chloropropyonyl chloride (Acros) followed by cyclization of the formed acylation product in H$_2$SO$_4$ (Reachim, Russia) as described in [Woodward, R. B.; Hoye, T. R. *J. Am. Chem. Soc.* 1977, 99, 8007].

Analytical and semi-preparative liquid chromatography was performed using Waters Delta 600 HPLC system including 996 Photodiode Array Detector, Nova-Pack C18 or HR Silica (60 A, 6 µm, 3.9 and 19×300 mm) and Symmetry C18 (5 µm, 4.6×250 mm) columns. $^{1}$H NMR spectra were recorded with a Bruker Avance-400 for 1-10% solutions in deuterated solvents. Chemical shifts for $^{1}$H were measured relatively to TMS. The assignment was made on the evidence of double resonance and NOE experiments. C, H microanalyses were done using CHN—O-Rapid analyzer (Heracus).

Catalyst 1

Rac- and meso-1,1'-Dimethylsilylene-bis[2-isobutyl-4-(4-tert-butylphenyl)-5,6,7-trihydro-s-indacenyl] zirconium dichlorides Preparation Example 1

Ethyl 2-acetyl-4-methylpentanoate

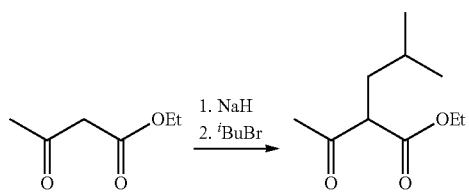

To a solution of 100 g (0.77 mol) of ethyl acetoacetate in 500 ml of DMF 30.7 g (0.77 mol) of 60% suspension of NaH in mineral oil was added in small portions by vigorous stirring at 60° C. This mixture was additionally stirred for 1 h, and then 105.5 g (0.77 mol) of isobutylbromide was added. The resulting mixture was stirred for 3 h at 90° C., then cooled to room temperature, and 1500 ml of cold water was added. The product was extracted by 3×300 ml of dichloromethane. The combined organic extract was evaporated at reduced pressure using rotary evaporator. Fractional rectification of the residue gave the title product, b.p. 75-80° C./4 mm Hg. Yield 80.5 g (56%).

Anal. calc. for $C_{10}H_{18}O_3$: C, 64.49; H, 9.74. Found: C, 64.20; H, 3.81.

$^1$H NMR (CDCl$_3$): δ 4.13 (q, J=7.2 Hz, 2H, CH$_2$Me), 3.44 (dd, J=8.3 Hz, J=6.6 Hz, 1H, CHCOMe), 2.16 (s, 3H, COMe), 1.74 (m, 1H, CHH"Pr), 1.62 (CHH"Pr), 1.47 (sept, J=6.6 Hz, 1H, CHMe$_2$), 1.21 (t, J=7.2 Hz, 3H, CH$_2$Me), 0.85 (d, J=6.6 Hz, 6H, CHMe$_2$).

Preparation Example 2

Ethyl 2-isobutylacrylate

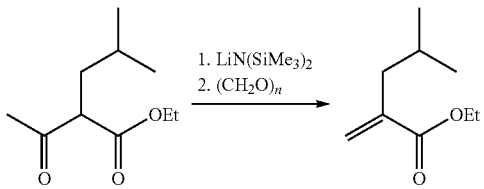

Bis(trimethylsilyl)amine (9.50 g, 59.0 mmol) in 250 ml of THF was metallated by 23.5 ml (59.0 mmol) of 2.5 M "BuLi in hexanes at −78° C. This mixture was additionally stirred for 0.5 h at room temperature, then cooled again to −78° C., and 10.0 g (53.7 mmol) of ethyl 2-acetyl-4-methylpentanoate was added. The resulting mixture was stirred for 1 h at room temperature, cooled to −78° C., and 8.0 g (09.27 mmol) of paraformaldehyde was added. This mixture was stirred overnight at room temperature, then filtered through glass frit (G3), and evaporated to dryness. Fractional rectification of the residue gave the title product, 50-55° C./4 mm Hg. Yield 6.50 g (78%).

Anal. calc. for $C_9H_{16}O_2$: C, 69.02; H, 10.32. Found: C, 69.09; H, 10.24.

$^1$H NMR (CDCl$_3$): δ 6.11 (m, 1H, =CHH'), 5.43 (m, 1H, =CHH'), 4.15 (q, J=7.1 Hz, 2H, CH$_2$Me), 2.14 (m, 2H, CH$_2$$^i$Bu), 1.75 (sept, J=6.7 Hz, 1H, CHMe$_2$) 1.25 (t, J=7.1 Hz, 3H, CH$_2$Me), 0.85 (d, J=6.7 Hz, 6H, CHMe$_2$).

Preparation Example 3

2-Isobutylacrylic acid

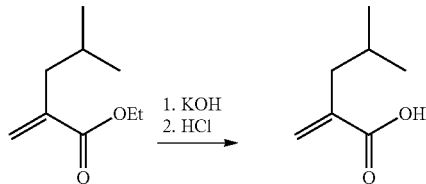

Saponification of 6.32 g (40.4 mmol) ethyl 2-isobutylacrylate was carried out 50 ml of 20% aqueous KOH at reflux. The obtained mixture was acidified by aqueous HCl to pH=5-6, and the product was extracted by 2×100 ml of dichloromethane. The organic extract was evaporated to dryness to give 5.13 g (99%) 2-isobutylacrylic acid which was further used without an additional purification.

Preparation Example 4

2-Isobutyl-3,5,6,7-tetrahydro-s-indacen-1(2H)-one

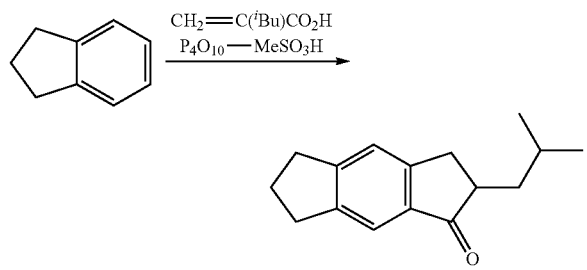

A mixture of 16.8 g (0.14 mol) of indane and 20.0 g (0.16 mmol) of 2-isobutylacrylic acid was added top a mixture of 40 g of P$_4$O$_{10}$ and 200 ml of methanesulfonic acid by vigorous stirring at 60° C. This mixture was additionally stirred at this temperature, and the resulting mixture was poured on 500 cm$^3$ of ice. The product was extracted by 3×200 ml of dichloromethane. The combined organic extract was washed by aqueous NaHCO$_3$, died over Na$_2$SO$_4$, and evaporated to dryness. The product was isolated by flash chromatography on silica gel 60 (40-63 um, eluent: hexanes-dichloromethane=3: 1, vol.). Yield 15.5 g (50%) of the title product.

Anal. calc. for $C_{16}H_{20}O$: C, 84.16; H, 8.83. Found: C, 84.25; H, 8.88.

$^1$H NMR (CDCl$_3$): δ 7.69 (s, 1H, 8H), 7.28 (s, 1H, 4H), 3.28 (m, 1H), 3.03-2.89 (m, 4H), 2.72 (m, 2H), 2.23-2.06 (m, 2H), 1.84 (m, 2H), 1.31 (m, 1H), 0.95 (d, J=6.3 Hz, 6H, CHMe$_2$).

Preparation Example 5

2-isobutyl-4-Bromo-3,5,6,7-tetrahydro-s-indacen-1 (2H)-one

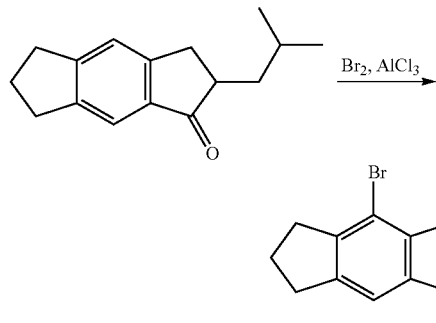

To a suspension of 14.6 g (110 mmol) of AlCl$_3$ in 40 ml of dichloromethane a solution of 10.0 g (43.8 mmol) of 2-isobutyl-3,5,6,7-tetrahydro-s-indacen-1(2H)-one in 25 ml of dichloromethane was added dropwise by vigorous stirring at 0° C. Further on, 7.71 g (48.2 mmol) of bromine was added dropwise at this temperature. The resulting mixture was stirred overnight at room temperature and then poured on 500 cm$^3$ of ice. The product was extracted by 3×200 ml of dichloromethane. The combined organic extract was washed by water, aqueous NaHCO$_3$, dried over Na$_2$SO$_4$, and evaporated to dryness. The product was isolated by flash chromatography on silica gel 60 (40-63 um, eluent: hexanes-dichloromethane=3:1, vol.). Yield 9.40 g (70%) of the title product.

Anal. calc. for $C_{16}H_{19}BrO$: C, 62.55; H, 6.23. Found: C, 62.70; H, 6.32.

$^1$H NMR (CDCl$_3$): δ 7.48 (s, 1H, 8-H), 3.21 (m, 1H), 2.95-3.05 (m, 4H), 2.72 (m, 1H), 2.64 (m, 1H), 2.15-2.10 (m, 2H), 1.87-1.77 (m, 2H), 1.30 (m, 1H), 0.97 (d, J=5.8 Hz, 6H, CHMe$_2$).

Preparation Example 6

4/8-Bromo-6-isobutyl-1,2,3,5-tetrahydro-s-indacene

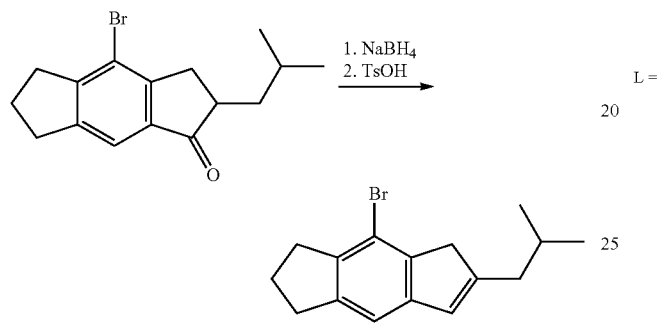

To a solution of 7.40 g (32.4 mmol) of 4-bromo-2-isobutyl-3,5,6,7-tetrahydro-s-indacen-1(2H)-one in 100 ml of a mixture of THF and methanol (2:1, vol.) 3.50 g (92.5 mmol) of NaBH$_4$ was added in small portions by vigorous stirring for 30 min at 0° C. This mixture was stirred overnight at room temperature and then evaporated to dryness. The product was extracted by 2×150 ml of dichloromethane. The combined organic extract was dried over Na$_2$SO$_4$ and then evaporated to dryness. To a solution of the residue in 100 ml of toluene 350 mg of TsOH was added, and the resulting mixture was refluxed for 3 h. The product was isolated by flash chromatography on silica gel 60 (40-63 um, eluent: hexanes). Yield 5.30 g (76%) of a ca. 1:5 mixture of 4-bromo-6-isobutyl-1,2,3,5-tetrahydro-s-indacene and 8-bromo-6-isobutyl-1,2,3,5-tetrahydro-s-indacene.

Anal. calc. for $C_{16}H_{19}Br$: C, 65.99; H, 6.58. Found: C, 54.15; H, 6.59.

$^1$H NMR (CDCl$_3$), 8-bromo-6-isobutyl-1,2,3,5-tetrahydro-s-indacene: δ 7.09 (s, 1H, 4-H in tetrahydroindacene), 6.61 (m, 1H, 3-H in tetrahydroindacene), 3.28 (s, 2H, 1,1'-H in tetrahydroindacene), 3.05 (m, 2H, CH$_2$CH$_2$CH$_2$), 3.00 (m, 2H, CH$_2$CH$_2$CH$_2$), 2.38 (m, 2H, CH$_2$CH$_2$CH$_2$), 2.15 (m, 2H, CH$_2^i$Bu), 1.95 (sept, J=6.7 Hz, 1H, CHMe$_2$), 0.98 (d, J=6.7 Hz, 6H, CHMe$_2$).

Preparation Example 7

4/8-(4-tert-Butylphenyl)-6-isobutyl-1,2,3,5-tetrahydro-s-indacene

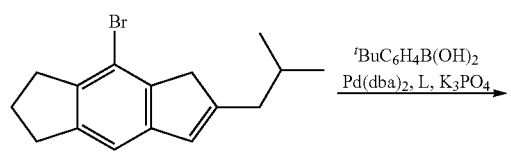

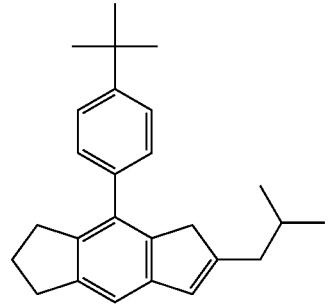

In argon atmosphere, a mixture of 2.13 g (12.0 mmol) of 4-tert-butylphenylboronic acid, 2.90 g (9.96 mmol) of 4/8-bromo-6-isobutyl-1,2,3,5-tetrahydro-s-indacene, 6.37 g (30.0 mmol) of K$_3$PO$_4$, 100 mg (0.17 mmol) of Pd(dba)$_2$, 150 mg (0.36 mmol) of dicyclohexyl(2',6'-dimethoxybiphenyl-2-yl)phosphine, and 30 ml of dry toluene was stirred for 12 h at 100° C. To the cooled resulting mixture 100 ml of cold water was added. The product was extracted by 3×100 ml of dichloromethane. The combined organic extract was dried over Na$_2$SO$_4$ and then evaporated to dryness. The product was isolated by flash chromatography on silica gel 60 (40-63 um, eluent: hexanes). Yield 3.40 g (98%) of a ca. 1:5 mixture of 4-(4-tert-butylphenyl)-6-isobutyl-1,2,3,5-tetrahydro-s-indacene and 8-(4-tert-butylphenyl)-6-isobutyl-1,2,3,5-tetrahydro-s-indacene.

Anal. calc. for $C_{26}H_{32}$: C, 90.64; H, 9.36. Found: C, 90.57; H, 9.49.

$^1$H NMR (CDCl$_3$), 8-(4-tert-butylphenyl)-6-isobutyl-1,2,3,5-tetrahydro-s-indacene: δ 7.47 (m, 2H, 2,6-H in 4-$^i$BuC$_6$H$_4$), 7.36 (m, 2H, 3,5-H in 4-$^i$BuC$_6$H$_4$), 7.18 (s, 1H, 4-H in tetrahydroindacene), 6.53 (m, 1H, 3-H in tetrahydroindacene), 3.23 (s, 2H, 1,1'-H in tetrahydroindacene), 3.01 (m, 2H, CH$_2$CH$_2$CH$_2$), 2.84 (m, 2H, CH$_2$CH$_2$CH$_2$), 2.33 (d, J=7.2 Hz, 2H, CH$_2^i$Bu), 2.16-2.04 (m, 2H, CH$_2$CH$_2$CH$_2$), 1.87 (m, 1H, CHMe$_2$), 1.42 (s, 9H, $^t$Bu), 0.93 (d, J=6.6 Hz, 6H, CHMe$_2$).

Preparation Example 8

A mixture of rac- and meso-bis[2-isobutyl-4-(4-tert-butylphenyl)-1,5,6,7-tetrahydro-s-indacen-1-yl](dimethyl)silanes

Preparation Example 9

Rac- and meso-1,1'-Dimethylsilylene-bis[2-isobutyl-4-(4-tert-butylphenyl)-5,6,7-trihydro-s-indacenyl] zirconium dichlorides

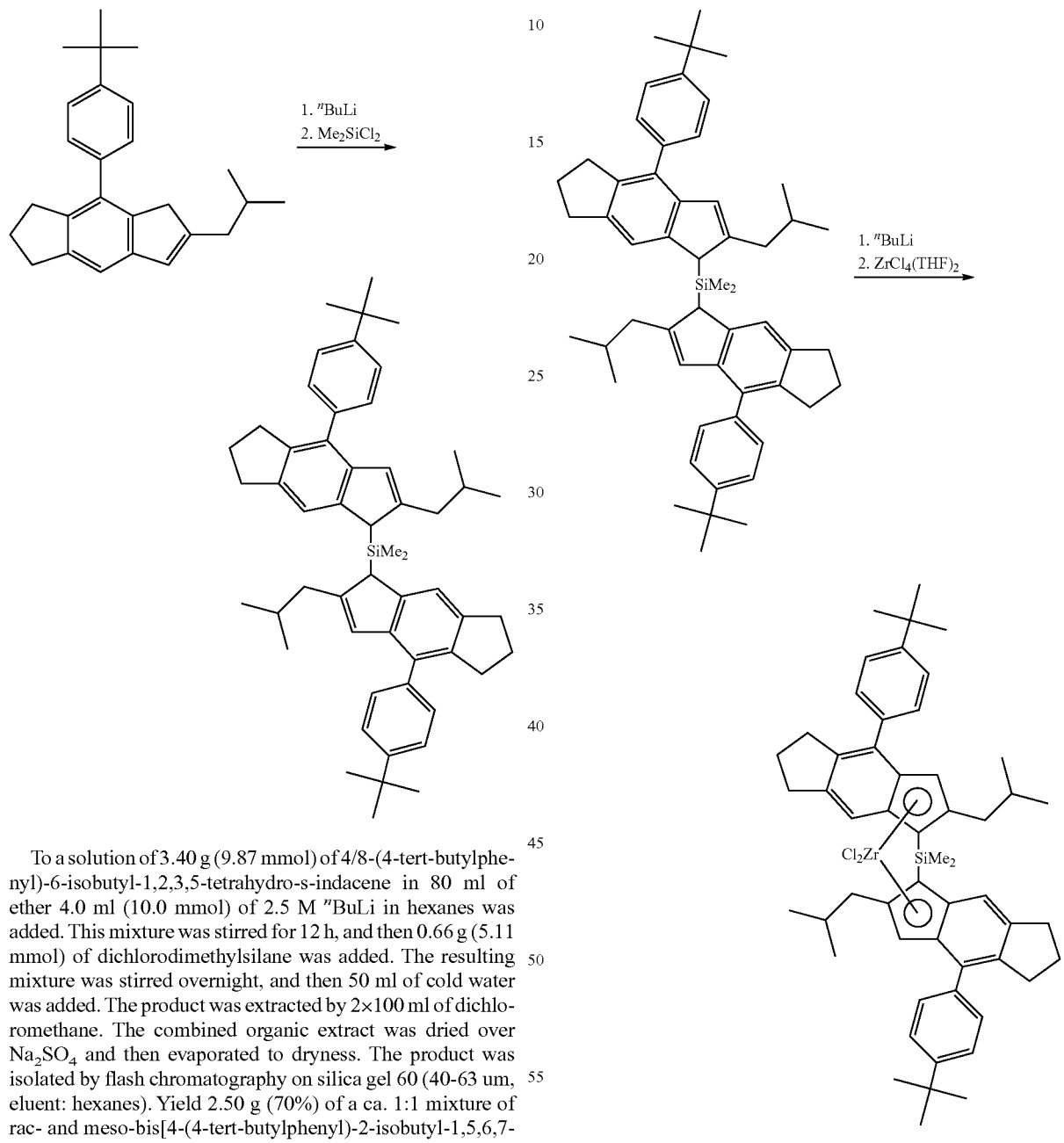

To a solution of 3.40 g (9.87 mmol) of 4/8-(4-tert-butylphenyl)-6-isobutyl-1,2,3,5-tetrahydro-s-indacene in 80 ml of ether 4.0 ml (10.0 mmol) of 2.5 M $^n$BuLi in hexanes was added. This mixture was stirred for 12 h, and then 0.66 g (5.11 mmol) of dichlorodimethylsilane was added. The resulting mixture was stirred overnight, and then 50 ml of cold water was added. The product was extracted by 2×100 ml of dichloromethane. The combined organic extract was dried over $Na_2SO_4$ and then evaporated to dryness. The product was isolated by flash chromatography on silica gel 60 (40-63 um, eluent: hexanes). Yield 2.50 g (70%) of a ca. 1:1 mixture of rac- and meso-bis[4-(4-tert-butylphenyl)-2-isobutyl-1,5,6,7-tetrahydro-s-indacen-1-yl](dimethyl)silanes.

Anal. calc. for $C_{54}H_{68}Si$: C, 87.03; H, 9.20. Found: C, 87.19; H, 9.35.

$^1$H NMR (CDCl$_3$): δ 7.46-7.42 (m, 8H), 7.39-7.34 (m, 8H), 7.26 (m, 2H), 7.23 (m, 2H), 6.58 (m, 4H), 3.74 (m, 4H), 3.12-2.78 (m, 16H), 2.46-2.24 (m, 8H), 2.04 (m, 8H), 1.94-1.75 (m, 4H), 1.40 (s, 18H), 1.39 (s, 18H), 0.92 (d, J=6.6 Hz, 6H), 0.89 (d, J=6.6 Hz, 6H), 0.83 (d, J=6.6 Hz, 6H), 0.81 (d, J=6.6 Hz, 6H), −0.17 (s, 3H), −0.22 (s, 6H), −0.30 (s, 3H).

To a solution of 2.98 g (4.0 mmol) of bis[4-(4-tert-butylphenyl)-2-isobutyl-1,5,6,7-tetrahydro-s-indacen-1-yl](dimethyl)silane in 60 ml of ether 3.20 ml (8.0 mmol) of 2.5 M $^n$BuLi in hexanes was added. This mixture was stirred for 12 h, then cooled to −60° C., and 1.51 g (4.0 mmol) of ZrCl$_4$(THF)$_2$ was added. The resulting mixture was stirred for 12 h at room temperature. Further on, this mixture was evaporated to dryness, and 40 ml of toluene was added. The formed suspension was stirred for 5 h at 60° C., and then this hot mixture filtered through glass frit (G4). The precipitate was additionally washed by 10 ml of hot toluene. The combined filtrate was evaporated to the reduced volume (ca. 20 ml) and then heated to 110° C. to dissolve some solid product. Orange crystals precipitated from this solution at room temperature were collected, washed by 5 ml of cold toluene, 10 ml of hexanes, and then dried in vacuum. This procedure gave 480 mg (13%) of pure meso-complex. The mother liquid was evaporated to dryness. The residue dried in vacuum was dissolved in 15 ml of ether. Yellow crystals precipitated from this solution at −30° C. were collected, washed by 5 ml of cold ether, and dried in vacuum. This procedure gave 180 mg (5%) of pure rac-complex.

Rac-Complex:

Anal. calc. for $C_{54}H_{66}Cl_2SiZr$: C, 71.64; H, 7.35. Found: C, 71.49; H, 7.45.

$^1$H NMR ($CD_2Cl_2$): δ 7.43-7.48 (m, 10H, 8-H in tetrahydroindacenyl and 2,3,5,6-H in $^tBuC_6H_4$), 6.65 (s, 2H, 3-H in tetrahydroindacenyl), 3.00-2.77 (m, 8H, $CH_2CH_2CH_2$), 2.64 (dd, J=13.8 Hz, J=7.0 Hz, 2H, CHH"Bu), 2.08 (dd, J=13.8 Hz, J=7.5 Hz, 2H, CHH"Bu), 1.98 (m, 4H, $CH_2CH_2CH_2$), 1.69 (m, 2H, CHMe₂), 1.35 (s, 18H, $^tBu$), 1.30 (s, 6H, SiMe₂), 0.86 (d, J=6.6 Hz, 6H, CHMeMe'), 0.78 (d, J=6.6 Hz, 6H, CHMeMe').

Meso-Complex:

Anal. calc. for $C_{54}H_{66}Cl_2SiZr$: C, 71.64; H, 7.35. Found: C, 71.60; H, 7.42.

$^1$H NMR ($CD_2Cl_2$): δ 7.50 (s, 2H, 8-H in tetrahydroindacenyl), 7.44 (m, 4H, 2,6-H in tetrahydroindacenyl), 7.40 (m, 4H, 3,5-H in tetrahydroindacenyl), 6.49 (s, 2H, 3-H in tetrahydroindacenyl), 2.95-2.65 (m, 8H, $CH_2CH_2CH_2$), 2.61 (dd, J=13.5 Hz, J=6.3 Hz, 2H, CHH"Bu), 2.44 (dd, J=13.5 Hz, J=8.0 Hz, 2H, CHH"Bu), 1.87 (m, 4H, $CH_2CH_2CH_2$), 1.47 (s, 3H, SiMeMe'), 1.35 (s, 18H, $^tBu$), 1.18 (s, 3H, SiMeMe'), 0.90 (d, J=6.6 Hz, 6H, CHMeMe'), 0.81 (d, J=6.6 Hz, 6H, CHMeMe').

Catalyst 2

Rac-1,1'-dimethylsilylene-bis[2-(cyclohexylmethyl)-4-(4-tert-butylphenyl)-5,6,7-trihydro-s-indacen-1-yl] zirconium dichloride Preparation Example 10

2-(Cyclohexylmethyl)-3,5,6,7-tetrahydro-s-indacen-1(2H)-one

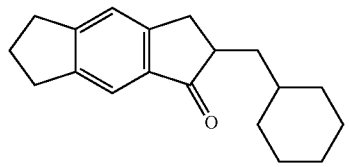 [SMILES: O=C1c2cc3c(cc2CC1CC1CCCCC1)CCC3]

In argon atmosphere, a 250 ml Berghof stainless steel autoclave with PTFE leaner was charged with 25.0 g (0.145 mol) of 3,5,6,7-tetrahydro-s-indacen-1(2H)-one, 20.0 g (0.178 mmol) of cyclohexanecarbaldehyde, 2.0 g (0.036 mol) of potassium hydroxide, 2.0 g of 10% Pd on charcoal and 150 ml of 96% ethanol. This reactor was flashed by hydrogen, and then hydrogen was fed to a pressure of 3 atm. This mixture was stirred for 3 h at room temperature. The resulting mixture was filtered through glass frit (G3), and the precipitate was additionally washed by 50 ml of ethanol. The filtrate was evaporated to dryness, and 500 ml was added to the residue. The crude product was extracted by 3×200 ml of dichloromethane. The combined organic extract was dried over $Na_2SO_4$ and then evaporated to dryness. The product was isolated by flash chromatography on silica gel 60 (40-63 um, eluent: dichloromethane). Yield 36.5 g (94%).

Anal. calc. for $C_{19}H_{24}O$: C, 85.03; H, 9.01. Found: C, 85.17; H, 8.90.

$^1$H NMR (CDCl₃): δ 7.59 (s, 1H, 8-H in tetrahydroindacene), 7.28 (s, 1H, 4-H in tetrahydroindacene), 3.27 (m, 1H, 2-H in tetrahydroindacene), 2.95 (m, 4H, 5,5',7,7'-H in tetrahydroindacene), 2.71-2.79 (m, 2H, 6,6'-H in tetrahydroindacene), 2.14 (m, 2H, 3,3'-H in tetrahydroindacene), 1.66-1.92 (m, 4H, two CH₂ groups in cyclohexyl), 1.48 (m, 1H, 1-H in cyclohexyl), 1.17-1.34 (m, 6H, three CH₂ groups in cyclohexyl), 1.00 (m, 2H, $CH_2C_6H_{11}$-c).

Preparation Example 11

2-(cyclohexylmethyl)-4-Bromo-3,5,6,7-tetrahydro-s-indacen-1(2H)-one

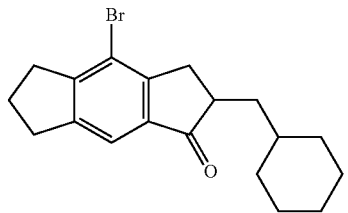 [SMILES: O=C1c2cc3c(c(Br)c2CC1CC1CCCCC1)CCC3]

To a mixture of 40.9 g (0.305 mol) of $AlCl_3$ in 180 ml of dichloromethane 32.7 g (0.122 mol) of 2-(cyclohexylmethyl)-3,5,6,7-tetrahydro-s-indacen-1(2H)-one was added. To this mixture cooled to 0° C. 21.5 g (0.134 mol) of bromine was added dropwise by vigorous stirring for 45 min at 0-5° C. The resulting mixture was stirred for 12 h at ambient temperature and then poured on 1000 cm³ of ice. The organic layer was separated, and the aqueous layer was extracted with 3×200 ml of dichloromethane. The combined organic extract was dried over $Na_2SO_4$ and then evaporated to dryness. This product was further used without an additional purification. Yield 39.5 g (93%).

Anal. calc. for $C_{19}H_{23}BrO$: C, 65.71; H, 6.68. Found: C, 65.53; H, 6.58.

$^1$H NMR (CDCl₃): δ 7.39 (s, 1H, 8-H in tetrahydroindacene), 3.11 (dd, J=17.4 Hz, J=7.8 Hz, 1H, 3-H in tetrahydroindacene), 2.94 (m, 2H, 7-CH₂ in tetrahydroindacene), 2.89 (m, 2H, 5-CH₂ in tetrahydroindacene), 2.66 (m, 1H, 2-H in tetrahydroindacene), 2.55 (dd, J=17.4 Hz, J=3.8 Hz, 1H, 3'-H in tetrahydroindacene), 2.05 (m, 2H, 6,6'-H in tetrahydroindacene), 1.54-1.79 (m, 4H, two CH₂ groups in cyclohexyl), 1.38 (m, 1H, 1-H in cyclohexyl), 0.72-1.23 (m, 8H, three CH₂ groups in cyclohexyl and $CH_2C_6H_{11}$-c).

Preparation Example 12

4-Bromo-6-(cyclohexylmethyl)-1,2,3,5-tetrahydro-s-indacene

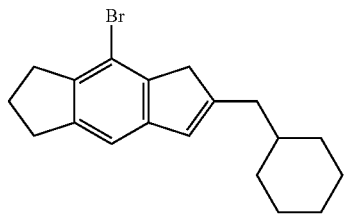 [SMILES: Brc1c2c(cc3c1CCC3)C=C(CC1CCCCC1)C2]

To a solution of 39.5 g (0.114 mol) of 4-bromo-2-(cyclohexylmethyl)-3,5,6,7-tetrahydro-s-indacen-1(2H)-one in 170 ml of THF 15.2 g (0.398 mol) of NaBH$_4$ was added. Further on, 340 ml of methanol was added dropwise by vigorous stirring for 2 h. The resulting mixture was stirred for 12 h at room temperature, evaporated to a volume of ca. 300 ml, and then 100 ml of 3.0 M HCl was added. The product was extracted with 3×200 ml of dichloromethane. The organic extract was dried over Na$_2$SO$_4$ and then evaporated to dryness. A solution of the residue and 1.4 g of TsOH in 800 ml of toluene was refluxed for 30 min with Dean-Stark head. The obtained solution was passed through short layer (50 mm) of silica gel 60 (40-63 um), the filtrate was evaporated to dryness. This procedure gave 34.7 g (93%) of the title product which was further used without an additional purification.

Anal. calc. for C19H$_{23}$Br: C, 68.88; H, 7.00. Found: C, 68.69; H, 6.85.

$^1$H NMR (CDCl$_3$): δ 7.03 (s, 1H, 4-H in tetrahydroindacene), 6.45 (m, 1H, 3-H in tetrahydroindacene), 3.23 (s, 2H, 1,1'-H in tetrahydroindacene), 3.00 (m, 2H, 5-CH$_2$ in tetrahydroindacene), 2.95 (m, m, 2H, 7-CH$_2$ in tetrahydroindacene), 2.34 (d, J=7.1 Hz, 2H, CH$_2$C$_6$H$_{11}$-c), 2.10 (m, 2H, 6,6'-H in tetrahydroindacene), 1.62-1.76 (m, 4H, two CH$_2$ groups in cyclohexyl), 1.54 (m, 1H, 1-H in cyclohexyl), 0.79-1.44 (m, 6H, three CH$_2$ groups in cyclohexyl).

Preparation Example 13

4-(4-tert-Butylphenyl)-6-(cyclohexylmethyl)-1,2,3,5-tetrahydro-s-indacene

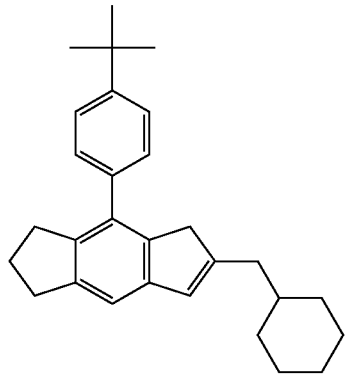 [SMILES: CC(C)(C)c1ccc(-c2c3c(cc4c2CCC4)C=C(CC2CCCCC2)C3)cc1]

In argon atmosphere, a mixture of 34.6 g (105 mmol) of 4-bromo-6-(cyclohexylmethyl)-1,2,3,5-tetrahydro-s-indacene, 22.4 g (126 mmol) 4-tert-butylphenylboronic acid, 66.8 g (315 mmol) of K$_3$PO$_4$, 1.21 g (21 mmol) of Pd(dba)$_2$, 1.73 g (42 mmol) of dicyclohexyl(2',6'-dimethoxybiphenyl-2-yl)phosphine and 350 ml of toluene was stirred for 12 h at 100° C. The resulting mixture was cooled to room temperature, and then 600 ml of water was added. The organic layer was separated, and the aqueous layer was extracted with 3×100 ml of dichloromethane. The combined organic extract was dried over Na$_2$SO$_4$ and then evaporated to dryness. The target product was isolated by flash chromatography on silica gel 60 (40-63 um; eluent: hexanes). Yield 24.0 g (62%).

Anal. calc. for C29H$_{36}$: C, 90.57; H, 9.43. Found: C, 90.44; H, 9.54.

$^1$H NMR (CDCl$_3$): δ 7.44-7.47 (m, 2H, 2,6-H in C$_6$H$_4$$^t$Bu), 7.33-7.37 (m, 2H, 3,5-H in C$_6$H$_4$$^t$Bu), 7.15 (s, 1H, 4-H in tetrahydroindacene), 6.49 (m, 1H, 3-H in tetrahydroindacene), 3.21 (s, 2H, 1,1'-H in tetrahydroindacene), 2.99 (m, 2H, 5-CH$_2$ in tetrahydroindacene), 2.82 (m, 2H, 7-CH$_2$ in tetrahydroindacene), 2.31 (d, J=7.1 Hz, 2H, CH$_2$C$_6$H$_{11}$-c), 2.05 (m, 2H, 6,6'-H in tetrahydroindacene), 1.60-1.75 (m, 4H, two CH$_2$ groups in cyclohexyl), 1.49 (m, 1H, 1-H in cyclohexyl), 1.40 (s, 9H, $^t$Bu), 0.75-1.36 (m, 6H, three CH$_2$ groups in cyclohexyl).

Preparation Example 14

Bis[2-(cyclohexylmethyl)-4-(4-tert-butylphenyl)-1,5,6,7-tetrahydro-s-indacen-1-yl](dimethyl)silane

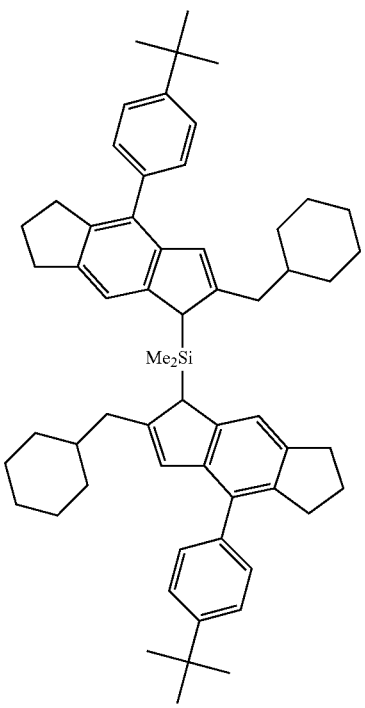

To a solution of 20.8 g (54.1 mmol) of 4-(4-tert-butylphenyl)-6-(cyclohexylmethyl)-1,2,3,5-tetrahydro-s-indacene in 600 ml of toluene 21.7 ml (54.2 mmol) of 2.5 M "BuLi in hexanes was added dropwise at 20° C. Then, 30 ml of THF was added, and the resulting mixture was stirred for 1 h at 70° C. The resulting mixture was cooled to 0° C., and 3.30 ml (3.49 g, 27.1 mmol) of dichlorodimethylsilane was added. This mixture was stirred for 12 h at room temperature, then 5 ml of water was added, and organic solvents were evaporated using Rotavapor. The product was extracted from the residue by 3×100 ml of dichloromethane. The organic extract was dried over Na$_2$SO$_4$ and then evaporated to dryness. The product was isolated by flash chromatography on silica gel 60 (40-63 um, eluent: hexanes and then hexanes-dichloromethane, 10:1, vol.). Yield 15.2 g (68%).

Anal. calc. for C$_{60}$H$_{76}$Si: C, 87.32; H, 9.28. Found: C, 87.23; H, 9.42.

$^1$H NMR (CDCl$_3$): δ 7.45-7.49 (m, 8H, 2,6-H in C$_6$H$_4$$^t$Bu of rac- and meso-), 7.35-7.41 (m, 8H, 3,5-H in C$_6$H$_4$$^t$Bu of rac- and meso-), 7.26 (s, 2H, 4-H in tetrahydroindacene of meso-), 7.22 (s, 2H, 4-H in tetrahydroindacene of rac-), 6.59 (br.s, 4H, 3-H in tetrahydroindacene rac- and meso-), 3.76 (s, 2H, 1-H in tetrahydroindacene of meso-), 3.74 (s, 2H, 1-H in tetrahydroindacene of rac-), 2.82-3.01 (m, 16H, 5,7-CH$_2$ in tetrahydroindacene of rac- and meso-), 2.32-2.48 (m, 8H, CH$_2$C$_6$H$_{11}$-c), 2.06 (m, 8H, 6,6'-H in tetrahydroindacene of rac- and meso-), 1.57-1.75 (m, 16H, two CH$_2$ groups in cyclohexyl of rac- and meso-), 1.42 (s, 18H, $^t$Bu of meso-), 1.41 (s, 18H, $^t$Bu of rac-), 0.77-1.32 (m, 28H, three CH$_2$ groups and 1-H in cyclohexyl of rac- and meso-), −0.14 (s, 3H, SiMeMe' of meso-), −0.18 (s, 3H, SiMe$_2$ of rac-), −0.30 (s, 3H, SiMeMe' of meso-).

Preparation Example 15 rac-1,1'-dimethylsilylene-bis[2-(cyclohexylmethyl)-4-(4-tert-butylphenyl)-5,6,7-trihydro-s-indacen-1-yl] zirconium dichloride

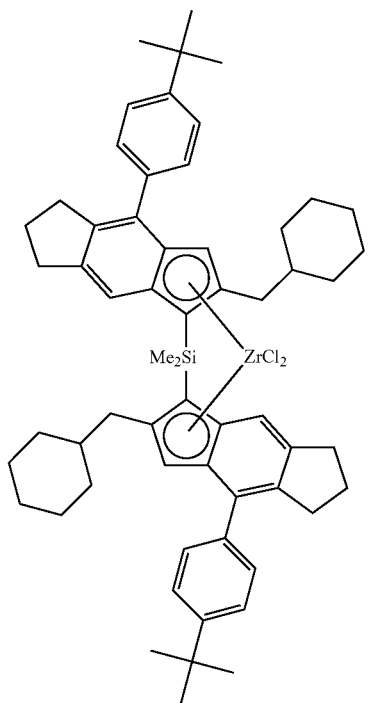

To a solution of 6.60 g (8.0 mmol) of bis[4-(4-tert-butylphenyl)-2-(cyclohexylmethyl)-1,5,6,7-tetrahydro-s-indacen-1-yl](dimethyl)silane in 150 ml of diethyl ether 6.40 ml (16.0 mmol) of 2.5 M $^n$BuLi in hexanes was added dropwise at 20° C. This mixture was stirred for 12 h at ambient temperature, then cooled to −78° C., and 3.02 g (8.0 mmol) of ZrCl$_4$(THF)$_2$ was added. The resulting mixture was stirred for 12 h at room temperature and then evaporated to dryness. The residue was dried in vacuum, and then 60 ml of toluene was added. The obtained suspension was stirred for 4 h at 60° C., then this hot mixture was filtered through Celite 503. The Celite layer was additionally washed by 20 ml of toluene. The combined filtrate was evaporated to a volume of ca. 40 ml. The formed suspension was heated to reflux in order to dissolve the precipitate. Crystals precipitated from this solution at room temperature were collected, washed by 3 ml of cold toluene, 5 ml of cold hexanes and then dried in vacuum. This procedure gave 0.91 g (11%) of pure rac-complex. The mother liquid was evaporated to a volume of ca. 20 ml. Again, this mixture was heated to reflux. Crystals precipitated at room temperature were collected, washed by 3 ml of cold toluene, 5 ml of cold hexanes and then dried in vacuum. This procedure gave 0.58 g of a ca. 10 to 1 mixture of rac- and meso-complexes. Crystallization of this mixture from hexanes-toluene (7:1, vol.) gave additional 0.45 g (5%) of pure rac-complex.

Anal. calc. for C60H$_{74}$Cl$_2$SiZr: C, 73.13; H, 7.57. Found: C, 73.28; H, 7.66.

$^1$H NMR (CD$_2$Cl$_2$): δ 7.46 (m, 8H, C$_6$H$_4$$^t$Bu), 7.44 (s, 2H, 8-H in tetrahydroindacene), 6.64 (s, 2H, 3-H in tetrahydroindacene), 2.76-3.04 (m, 8H, 5,5',7,7'-H in tetrahydroindacene), 2.65 (dd, J=13.9 Hz, J=6.8 Hz, 2H, CHH'C$_6$H$_{11}$-c), 2.07 (dd, J=13.9 Hz, J=7.6 Hz, 2H, CHH'C$_6$H$_{11}$-c), 1.98 (m, 4H, 6,6'-H in tetrahydroindacene), 1.60 (m, 8H, two CH$_2$ groups in cyclohexyl), 1.47 (m, 2H, 1-H in cyclohexyl), 1.35 (s, 18H, $^t$Bu), 1.30 (s, 6H, SiMe$_2$), 0.76-1.22 (m, 12H, three CH$_2$ groups in cyclohexyl).

Catalyst Preparation

MAO was purchased from Albemarle and used as a 30 wt-% solution in toluene. Perfluoroalkylethyl acrylate esters (CAS number 65605-70-1) were purchased from the Cytonix Corporation, dried and degassed prior to use. Hexadecafluoro-1,3-dimethylcyclohexane was dried and degassed prior to use.

Inventive Metallocene 1 rac-1,1'-dimethylsilylene-bis[2-isobutyl-4-(4-tert-butylphenyl)-5,6,7-trihydro-s-indacen-1-yl]zirconium dichloride

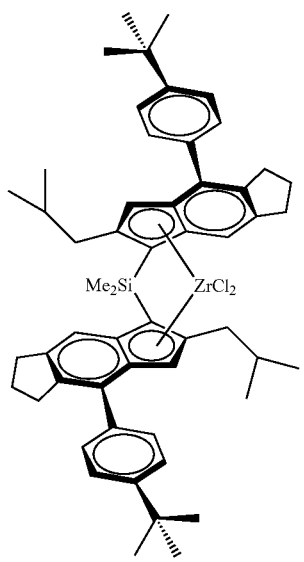

Inventive Metallocene 2 rac-1,1'-dimethylsilylene-bis[2-(cyclohexylmethyl)-4-(4-tert-butylphenyl)-5,6,7-trihydro-s-indacen-1-yl] zirconium dichloride

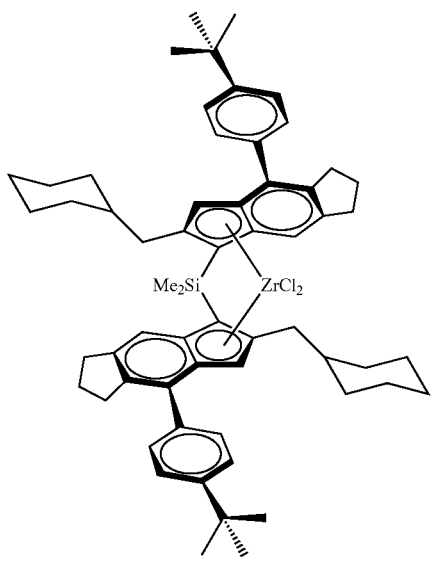

Comparative Metallocene 1 rac-1,1'-dimethylsilylene-bis[2-methyl-4-(4-tert-butylphenyl)-5,6,7-trihydro-s-indacen-1-yl]}zirconium dichloride) was prepared as described in WO2006/097497A1. Its $^1$H NMR spectrum corresponds to that reported in the mentioned patent application.

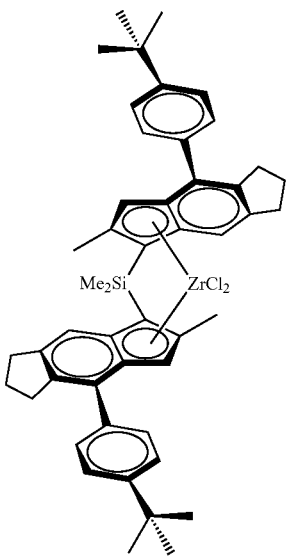

Comparative Metallocene 2 rac-1-cyclohexyl-1'-methylsilylene-bis[2-methyl-4-(4'-tert-butylphenyl)indenyl]zirconium dichloride) was obtained from a commercial source (CAS no 888227-55-2; WO2006/060544)

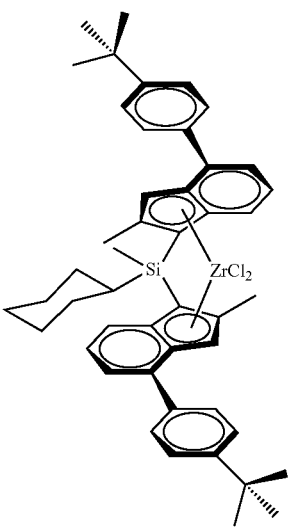

Example 1

E1

The catalyst was prepared according to the procedure described in the Example 5 of WO 2003/051934 with hexadecafluoro-1,3-dimethylcyclohexane as the immiscible solvent, a mixture of perfluoroalkylethyl acrylate esters having different perfluoroalkyl chain lengths as the surfactant precursor and rac-1,1'-dimethylsilylene-bis[2-isobutyl-4-(4-tert-butylphenyl)-5,6,7-trihydro-s-indacen-1-yl]zirconium dichloride as the metallocene.

The detailed catalyst preparation was performed as follows:

Inside a glovebox, 80 µL of a commercial mixture of dry and degassed perfluoroalkylethyl acrylate esters were mixed with 2 mL of MAO in a septum bottle and left to react overnight (surfactant solution). The following day, 68.80 mg of the metallocene (0.076 mmol, 1 equivalent) were dissolved in 4 mL of the MAO solution in another septum bottle and left to stir inside the glovebox (catalyst solution).

After 60 minutes, the 4 mL of the catalyst solution and 1 mL of the surfactant solution were successively added into a 50 mL emulsification glass reactor containing 40 mL of hexadecafluoro-1,3-dimethylcyclohexane at −10° C. and equipped with an overhead stirrer (stirring speed=600 rpm). A red-orange emulsion formed immediately (measured emulsion stability=15 seconds) and was stirred during 15 minutes at 0° C./600 rpm. The emulsion was then transferred via a 2/4 Teflon tube to 100 mL of hot hexadecafluoro-1,3-dimethylcyclohexane at 90° C., and stirred at 600 rpm until the transfer was completed. The stirring speed was reduced to 300 rpm and the oil bath was removed. Stirring was continued at room temperature for 15 more minutes. When the stirrer was switched off, the catalyst was left to settle up on top of the continuous phase which was siphoned off after 45 minutes. The remaining red solid catalyst was dried during 2 hours at 50° C. over an argon flow.

Example 2

E2

The catalyst was synthesised following the above described protocols of Example 1 with 0.076 mmol (1 equivalent, 74.90 mg) of rac-1,1'-dimethylsilylene-bis[2-(cyclohexylmethyl)-4-(4-tert-butylphenyl)-5,6,7-trihydro-s-indacen-1-yl]zirconium dichloride as the metallocene.

Comparative Example 1

CE1

The catalyst was synthesised following the above described protocols of Example 1 with 0.076 mmol (1 equivalent, 61.50 mg) of rac-1,1'-dimethylsilylene-bis[2-methyl-4-(4-tert-butylphenyl)-5,6,7-trihydro-s-indacen-1-yl]}zirconium dichloride as the metallocene.

Comparative Example 2

CE2

The catalyst was synthesised following the above described protocols of Example 1 with 0.076 mmol (1 equivalent, 61.50 mg) of rac-1-cyclohexyl-1'-methylsilylene-bis[2-methyl-4-(4'-tert-butylphenyl)indenyl]zirconium dichloride as the metallocene.

TABLE 1

Catalyst syntheses summary

| Code | Al(wt-%) | Zr(wt-%) | Al/Zr (molar) |
|------|----------|----------|---------------|
| E1   | 26.10    | 0.33     | 267           |
| E2   | 21.40    | 0.23     | 314           |
| CE1  | 25.20    | 0.32     | 267           |
| CE2  | 31.00    | 0.37     | 283           |

Polymerisations: Homopolymerisation of Propylene

Propylene was provided by Borealis and adequately purified before use. Triethylaluminum was purchased from Crompton and used in pure form. Hydrogen is provided by AGA and purified before use.

The polymerisations were performed in a 5 L reactor. 200 µl of triethylaluminum was fed as a scavenger in 5 mL of dry and degassed pentane. The desired amount of hydrogen was then loaded (measured in mmol) and 1100 g of liquid propylene was fed into the reactor. The temperature was set to 30° C. The desired amount of catalyst (5 to 30 mg) in 5 mL of hexadecafluoro-1,3-dimethylcyclohexane was then flushed into the reactor with a nitrogen overpressure and temperature raised to 70° C. over a period of 15 minutes. The polymerisation was stopped after 30 minutes by venting the reactor and flushing with nitrogen before the polymer was collected.

Polymerisation results are collected in Tables 2 and 3.

TABLE 2

Homo-PP polymerisation data.

| Exp. | Catalyst | Catalyst (mg) | $H_2$ (mmol) | Polymer (g) | Activity (kg/g/h) | Metal Activity (kg/g Zr/h) |
|------|----------|---------------|--------------|-------------|-------------------|----------------------------|
| 1    | E1       | 8.1           | 1            | 135         | 33                | 10091                      |
| 2    |          | 7.0           | 6            | 382         | 109               | 33061                      |
| 3    |          | 6.0           | 15           | 431         | 143               | 43545                      |
| 4    | E2       | 7.1           | 1            | 102         | 28                | 12478                      |
| 5    |          | 7.0           | 6            | 364         | 105               | 45870                      |
| 6    |          | 6.0           | 15           | 508         | 161               | 70130                      |
| 7    | CE1      | 7.2           | 1            | 133         | 36                | 11531                      |
| 8    |          | 6.5           | 6            | 300         | 92                | 28844                      |
| 9    |          | 6.9           | 15           | 438         | 127               | 39688                      |
| 10   | CE2      | 27.4          | 1            | 193         | 14                | 3811                       |
| 11   |          | 30.2          | 6            | 337         | 22                | 6027                       |
| 12   |          | 28.6          | 15           | 407         | 28                | 7703                       |

TABLE 3

Homo-PP analyses data.

| Exp. | Catalyst | $MFR_2$ (g/10 min) | $MFR_{21}$ (g/10 min) | $M_w$ exp. (kg/mol) | MWD | $T_m$ (° C.) | $T_c$ (° C.) | XS (%) |
|------|----------|--------------------|-----------------------|---------------------|-----|--------------|--------------|--------|
| 1    | E1       | —                  | 6.4                   | 723                 | 2.4 | 155.9        | 111.6        | 0.3    |
| 2    | E1       | 2.6                | —                     | 329                 | 2.2 | 155.6        | 112          | 0.2    |
| 3    | E1       | 32.                | —                     | 164                 | 2.4 | 155.4        | 114.7        | 0.2    |
| 4    | E2       | —                  | 3.5                   | 899                 | 2.4 | 155.7        | 112.3        | 0.3    |
| 5    | E2       | 3.3                | —                     | 300                 | 2.1 | 156.2        | 114.8        | 0.1    |
| 6    | E2       | 30.2               | —                     | 158                 | 2.4 | 155.6        | 115.8        | 0.1    |
| 7    | CE1      | —                  | 4.3                   | 802                 | 2.2 | 152.9        | 113.1        | —      |
| 8    | CE1      | 2.0                | —                     | 345                 | 2.3 | 154.8        | 111.7        | —      |
| 9    | CE1      | 17.4               | —                     | 187                 | 2.5 | 154.2        | 115.1        | —      |
| 10   | CE2      | 0.14               | 12.5                  | 665                 | 2.5 | 149.4        | 109.5        | —      |
| 11   | CE2      | 1.3                | —                     | 416                 | 2.1 | 150.6        | 109.9        | —      |
| 12   | CE2      | 12.3               | —                     | 222                 | 2.4 | 151.0        | 112.1        | —      |

TABLE 4

Homo-PP $^{13}C$ NMR data.

| Exp. | Catalyst | mm %  | 2.1e % | 3.1%  |
|------|----------|-------|--------|-------|
| 1    | E1       | 99.76 | 0.53   | 0.01  |
| 2    |          | 99.73 | 0.55   | 0.00  |
| 3    |          | 99.66 | 0.51   | 0.01  |
| 8    | CE1      | 99.60 | 0.70   | 0.00  |

Discussion

It can be seen from entries 1-3 and 4-6 of Table 2 that high activities are achieved with the catalysts of the invention E1 and E2. Under similar initial hydrogen loading, the catalysts of the invention E1 and E2 surpass the polymerisation catalysis performance of CE2, and also display, 10-25% higher activities than CE1 at higher hydrogen concentrations.

Also, the catalysts of the invention gives access to high molecular weight homo-PP polymers with high melting temperatures. These melting temperatures are higher than those of the polypropylene homopolymers obtained with CE1 displaying a similar molecular weight (entries 7-9 Table 3), and significantly higher than the ones from polymers produced by CE2 (entries 7-9 Table 3).

The invention claimed is:

1. A complex of formula (I):

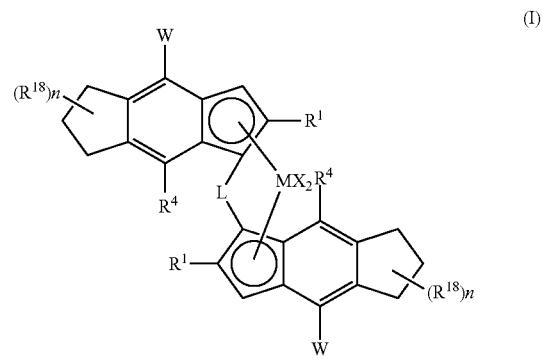

wherein
M is zirconium or hafnium;
each X is a sigma ligand;
L is a divalent bridge selected from —R'$_2$C—, —R'$_2$C—CR'$_2$—, —R'$_2$Si—, —R'$_2$Si—SiR'$_2$—, —R'$_2$Ge—, wherein each R' is independently a hydrogen atom, C1-C20-hydrocarbyl, tri(C1-C20-alkyl)silyl, C6-C20-aryl, C7-C20-arylalkyl or C7-C20-alkylaryl;
each $R^1$ is a C4-C20 hydrocarbyl radical branched at the β-atom to the cyclopentadienyl ring, optionally containing one or more heteroatoms belonging to groups 14-16, or is a C3-C20 hydrocarbyl radical branched at the β-atom to the cyclopentadienyl ring where the β-atom is an Si-atom;
n is 0-3;
each $R^{18}$ is the same or different and is a C1-C20 hydrocarbyl radical optionally containing one or more heteroatoms belonging to groups 14-16;
each $R^4$ is a hydrogen atom or a $C_{1-6}$-hydrocarbyl radical;
each W is a 5 or 6 membered aryl or heteroaryl ring wherein each atom of said ring is optionally substituted with an $R^5$ group;
each $R^5$ is the same or different and is a C1-C20 hydrocarbyl radical optionally containing one or more heteroatoms belonging to groups 14-16; and optionally two adjacent $R^5$ groups taken together can form a further mono or multicyclic ring condensed to W optionally substituted by one or two groups $R^5$.

2. A catalyst comprising
(i) a complex of formula (I) as defined in claim 1; and
(ii) a cocatalyst comprising an organometallic compound of a Group 13 metal.

3. A catalyst as claimed in claim 2 prepared by a process comprising
(I) forming a liquid/liquid emulsion system, said liquid/liquid emulsion system comprising a solution of the catalyst components (i) and (ii) dispersed in a solvent so as to form dispersed droplets; and
(II) solidifying said dispersed droplets to form solid particles.

4. A catalyst as claimed in claim 2 further comprising an inert carrier.

5. A complex of claim 1, wherein L is —SiR$^6{}_2$—, wherein each $R^6$ is independently C1-C20-alkyl, C6-C20-aryl or tri(C1-C20-alkyl)silyl-residue or ethylene bridge.

6. A complex of claim 1, wherein $R^1$ is the group —CH$_2$—$R^{1'}$ and $R^{1'}$ represents a C3-19 hydrocarbyl group optionally containing one or more heteroatoms belonging to groups 14-16, a C2-19 hydrocarbyl group where the β-atom to the cyclopentadienyl ring is an Si-atom, so as to provide a branch β to the cyclopentadienyl ring, a $C_{3-7}$-cycloalkyl group optionally substituted by $C_{1-6}$-alkyl, a $C_{6-10}$-aryl group, especially phenyl or an $C_{3-8}$-alkyl group such that the position β to cyclopentadienyl is branched.

7. A complex of claim 1, wherein n is 0.

8. A complex of claim 1, wherein $R^4$ is a hydrogen atom or methyl, ethyl, propyl or isopropyl group.

9. A complex of claim 1, wherein W is an optionally substituted phenyl group, or a 5 or 6 membered heteroaryl group selected from furanyl, thiophenyl, pyrrolyl, triazolyl, and pyridinyl.

10. A complex of claim 1, wherein $R^5$ is a linear or branched, cyclic or acyclic, C1-C10-alkyl group or two adjacent $R^5$ groups taken together form a further mono or multicyclic aromatic ring condensed to W.

11. A complex of claim 1, comprising a complex of formula (II):

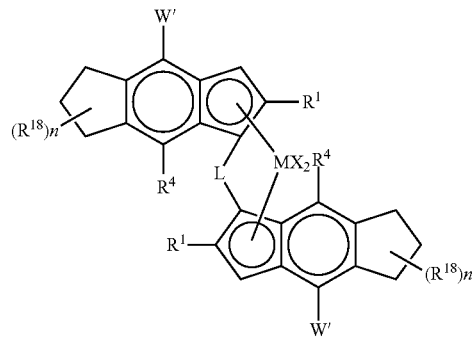

(II)

wherein
M is Zr or Hf;
each $R^1$ is CH$_2$-Ph, CH$_2$—C(R$^3$)$_{3-q}$(H)$_q$ wherein $R^3$ is a $C_{1-6}$-alkyl group or together two $R^3$ groups form a $C_{3-7}$-cycloalkyl ring wherein said ring is optionally substituted by a $C_{1-6}$ alkyl group and q can be 1 or 0;
L is ethylene or SiR$^6{}_2$;
$R^6$ is C1-10 alkyl, $C_{6-10}$-aryl, $C_{7-12}$-alkylaryl, or $C_{7-12}$-arylalkyl;
each X is a hydrogen atom, —OR, a halogen atom, or an R group;
R is $C_{1-10}$ alkyl
each $R^4$ is H or $C_{1-3}$-alkyl;
n is 0 to 3;
each W' is aryl (e.g. phenyl), pyridyl, thiophenyl, or furyl optionally substituted by up to 2 groups $R^5$;
each $R^5$ is $C_{1-10}$-alkyl or two adjacent $R^5$ groups taken together form a phenyl ring fused to W' or two adjacent $R^5$ groups taken together form the atoms necessary to form a carbazolyl group with the W' group; and
each $R^{18}$ is $C_{1-6}$-alkyl;
and wherein the two ligands forming the complex are identical.

* * * * *